(12) United States Patent
Janda et al.

(10) Patent No.: US 11,278,330 B2
(45) Date of Patent: Mar. 22, 2022

(54) IMPLANTABLE BONE ADJUSTMENT DEVICES

(71) Applicant: SMITH & NEPHEW, INC., Memphis, TN (US)

(72) Inventors: Haden Janda, Germantown, TN (US); Paul Bell, Memphis, TN (US); Daniel Farley, Memphis, TN (US); Sied W. Janna, Memphis, TN (US)

(73) Assignee: SMITH & NEPHEW, INC., Memphis, TN (US)

( * ) Notice: Subject to any disclaimer, the term of this patent is extended or adjusted under 35 U.S.C. 154(b) by 194 days.

(21) Appl. No.: 16/482,111

(22) PCT Filed: Jan. 29, 2018

(86) PCT No.: PCT/US2018/015731
§ 371 (c)(1),
(2) Date: Jul. 30, 2019

(87) PCT Pub. No.: WO2018/144386
PCT Pub. Date: Aug. 9, 2018

(65) Prior Publication Data
US 2020/0022741 A1    Jan. 23, 2020

Related U.S. Application Data

(60) Provisional application No. 62/453,749, filed on Feb. 2, 2017.

(51) Int. Cl.
*A61B 17/72* (2006.01)
*A61B 17/00* (2006.01)
*A61B 17/68* (2006.01)

(52) U.S. Cl.
CPC ...... *A61B 17/7216* (2013.01); *A61B 2017/00876* (2013.01); *A61B 2017/681* (2013.01)

(58) Field of Classification Search
CPC .......... A61B 17/7216; A61B 2017/681; A61B 17/7014; A61B 17/7016; A61B 17/7019
See application file for complete search history.

(56) References Cited

U.S. PATENT DOCUMENTS

| 4,931,055 | A | * | 6/1990 | Bumpus | ............. | A61B 17/7014 |
| | | | | | | 606/254 |
| 6,336,929 | B1 | * | 1/2002 | Justin | ................. | A61B 17/7216 |
| | | | | | | 606/63 |

(Continued)

FOREIGN PATENT DOCUMENTS

| WO | 2006/079184 A1 | 8/2006 |
| WO | 2008/129995 A1 | 10/2008 |

OTHER PUBLICATIONS

International Search Report and Written Opinion for International Patent Application PCT/US2018/015731, dated Apr. 25, 2018, 9 pages.

*Primary Examiner* — Lynnsy M Summitt
(74) *Attorney, Agent, or Firm* — Kacvinsky Daisak Bluni PLLC

(57) ABSTRACT

A reconfigurable bone adjustment device (1, 101, 201) includes a first member (10,110, 210, 1010) configured for attachment to a first bone fragment, a second member (20, 130, 230, 1030) configured for attachment to a second bone fragment and a reconfiguration assembly (2, 102, 401, 501, 601, 701, 801, 901, 1020) configured to move the second member relative to the first member. The reconfiguration assembly includes a drive mechanism (50, 150, 250, 440, 540, 640, 740, 840, 940, 1050) and a threaded rod (70, 170, 245, 470, 570, 670, 770, 870, 970, 1070, 1170) operatively coupled to the drive mechanism so that rotation of the drive mechanism rotates the threaded rod. The reconfiguration assembly operates to reduces stresses, forces, bending moments and/or eccentric moments on a junction and/or by (Continued)

configuring the junction in a manner whereby one of more of the forces, is isolated away from the junction.

24 Claims, 14 Drawing Sheets

(56) References Cited

U.S. PATENT DOCUMENTS

| | | | | |
|---|---|---|---|---|
| 6,849,076 B2* | 2/2005 | Blunn | ................ | A61B 17/7216 |
| | | | | 606/105 |
| 8,197,490 B2* | 6/2012 | Pool | ................... | A61B 17/7004 |
| | | | | 606/90 |
| 8,449,543 B2* | 5/2013 | Pool | ................... | A61B 17/1725 |
| | | | | 606/63 |
| 8,568,457 B2* | 10/2013 | Hunziker | ........... | A61B 17/7016 |
| | | | | 606/258 |
| 8,632,548 B2* | 1/2014 | Soubeiran | ............ | A61B 17/025 |
| | | | | 606/90 |
| 9,044,281 B2* | 6/2015 | Pool | ....................... | A61B 17/86 |
| 9,179,938 B2* | 11/2015 | Pool | ....................... | A61B 17/68 |
| 9,308,089 B2* | 4/2016 | Vicatos | ............... | A61B 17/7216 |
| 9,421,046 B2 | 8/2016 | Pool et al. | | |
| 10,463,406 B2* | 11/2019 | Chang | .................... | A61B 17/68 |
| 10,675,064 B2* | 6/2020 | Fening | ............... | A61B 17/7016 |
| 10,751,094 B2* | 8/2020 | Green | ............... | A61B 17/7055 |
| 10,918,425 B2* | 2/2021 | Schwardt | ............... | A61B 17/62 |
| 2014/0236311 A1* | 8/2014 | Vicatos | ............... | A61B 17/7216 |
| | | | | 623/23.47 |
| 2015/0105826 A1* | 4/2015 | Green | ................ | A61B 17/7055 |
| | | | | 606/263 |
| 2016/0008032 A1* | 1/2016 | Chang | ................... | A61B 17/68 |
| | | | | 606/62 |

\* cited by examiner

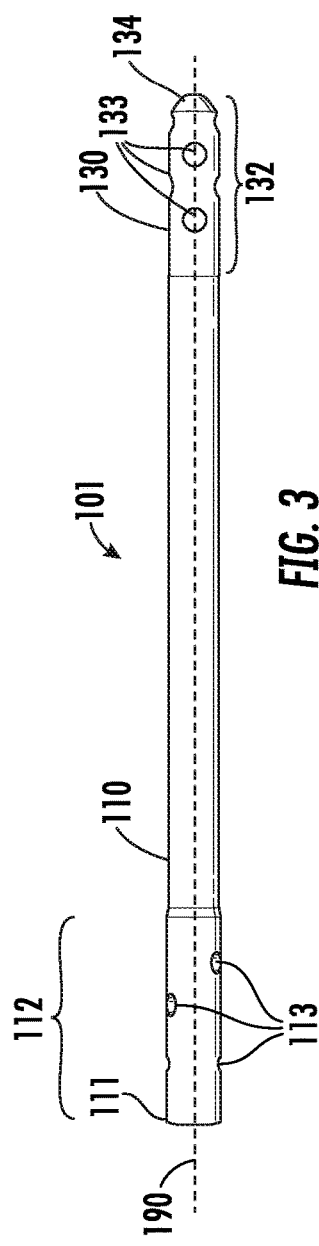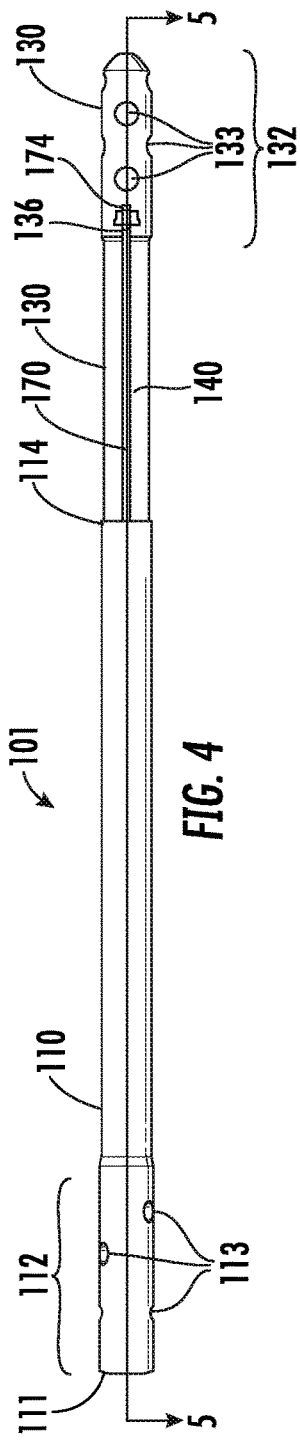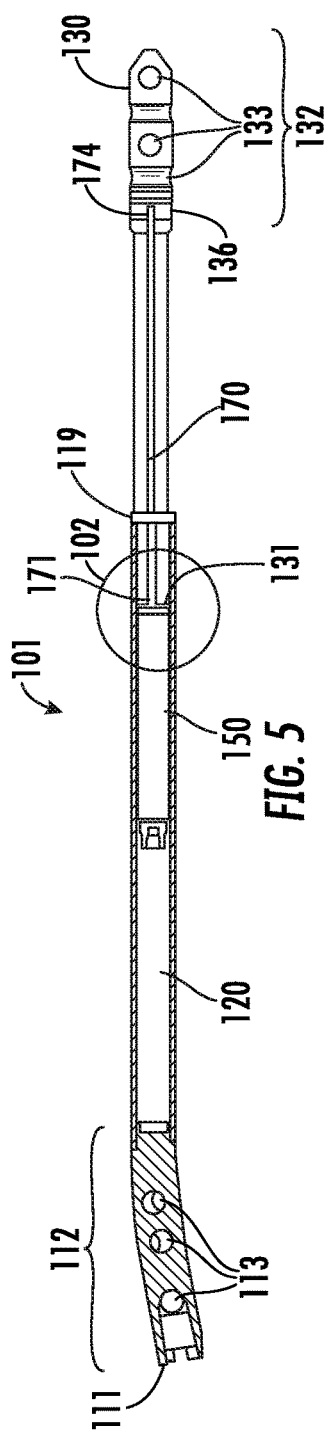

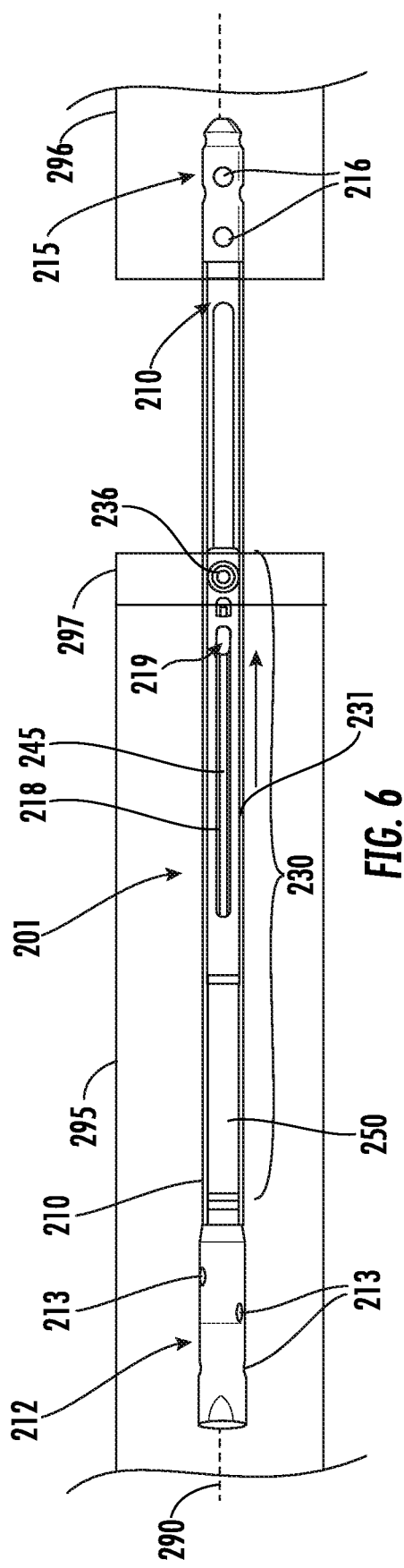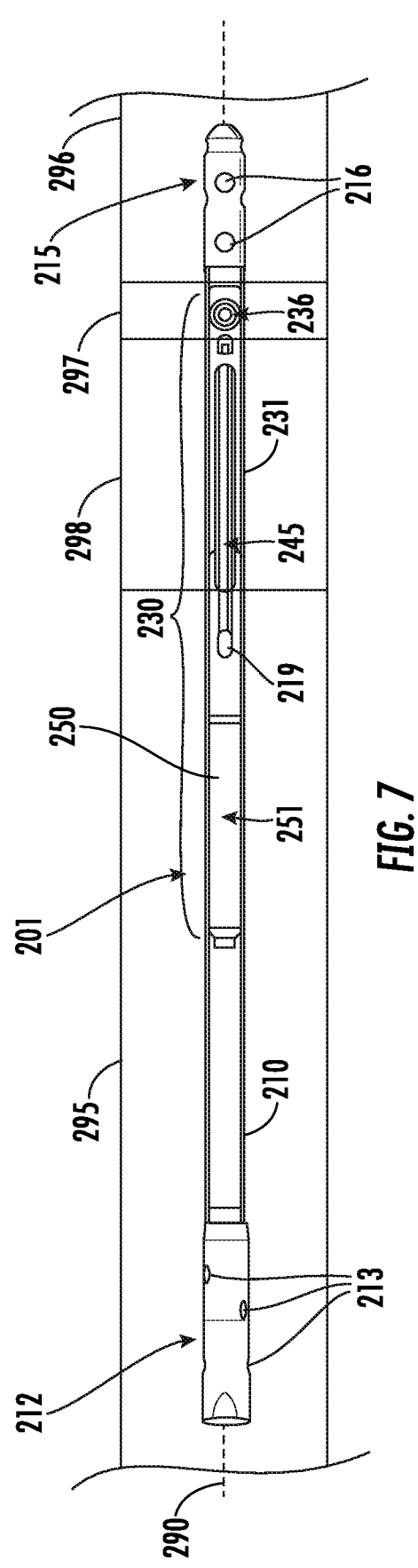

IMPLANTABLE BONE ADJUSTMENT DEVICES

CROSS-REFERENCE TO RELATED APPLICATIONS

This application is a United States National Phase filing of International Application No. PCT/US2018/015731, filed Jan. 29, 2018, which claims priority to U.S. Provisional Patent Application Ser. No. 62/453,749, entitled "Implantable Bone Adjustment Devices," filed Feb. 2, 2017, the entirety of each application is hereby incorporated by reference herein.

TECHNICAL FIELD

The present disclosure generally relates to implantable reconfigurable bone adjustment devices, and more particularly, but not exclusively, relates to implantable reconfigurable bone adjustment devices that include a reconfiguration assembly including a threaded rod rigidly coupled to a driver.

BACKGROUND

Implantable reconfigurable bone adjustment devices are occasionally used in orthopedic procedures to gradually adjust the position, orientation, geometry and/or length of a bone, such as, for example, by distraction, compression, realignment or bone transport. One form of an implantable reconfigurable bone adjustment device is a limb lengthening nail (LLN) configured for implantation in the medullary canal of a long bone and subsequently manipulated to adjust the length of the bone. Another form of an implantable reconfigurable bone adjustment device is a bone transport nail configured for implantation in the medullary canal of a long bone and subsequently manipulated to move a middle bone fragment across a gap between proximal and distal bone fragments to induce bone regeneration in the gap. Still other forms of implantable reconfigurable bone adjustment devices include spinal adjustment implants and implants configured to achieve other gradual adjustments to the shape, position or length of skeletal structures.

Implantable reconfigurable bone adjustment devices may include internal magnets that are configured to rotate upon actuation by an external actuating device, thereby driving a threaded rod that engages other device components to achieve a dimensional modification of the device or other relational modification between components of the device. Such dimensional modification or relational modification of the device operate on bone segments, portions or fragments to which the device is affixed to exert pressures on the bone segments, portions or fragments to which the device is affixed, thereby gradually moving the bone segments, portions or fragments relative to one another. Such devices may include a first member configured to be affixed to a first bone segment, portion or fragment; a second member configured to be affixed to another bone segment, portion or fragment; a rod with at least one thread, the rotation of which causes displacement of the second member relative to the first member, and a mechanism for controlling the rotation of the threaded rod. In the case of certain LLN devices, for example, the second member may be assembled telescopically relative to the first member and rotation of the threaded rod operates to telescopically displace the second member relative to the first member, thereby increasing the distance between the bone segments, portions or fragments to which the first member and the second member are respectively affixed. In the case of certain bone transport nails, the first member may have a first end configured to be affixed to a first bone fragment, a second end configured to be affixed to a second bone fragment, and a carriage configured to be affixed to a middle bone fragment positioned within a gap between the first and second bone fragments. Rotation of the threaded rod in such a device operates to axially transport the carriage relative to the first member to thereby facilitate formation of regenerate bone between the first and second bone fragments.

In such implantable reconfigurable bone adjustment devices, rotation of the threaded rod may be driven by a component, referred to herein as a "drive mechanism," whose actuation is controlled to achieve a desired amount of rotation over time and at a desired rate, thereby to achieve a desired amount of bone adjustment at a desired rate. In certain devices, the drive mechanism includes a magnet hermetically sealed in a housing, although other types of drive mechanisms, such as electric motors, are contemplated. A common feature of such drive mechanisms, which may also include gear reducers, is that the threaded rod is rigidly affixed to a structure of the drive mechanism to achieve controlled rotation of the threaded rod. This structure is referred to herein as a "driver."

The threaded rod in such devices necessarily engages at least one component of the device (other than the driver) such that rotation of the threaded rod changes the relative positions of different device components. The rotation of the threaded rod imposes forces on the threaded rod, which may differ in different regions of the threaded rod, such as axial loads (compressive and/or tensile), bending moments and the like. For example, in some such devices, the junction at which the threaded rod is connected to the driver carries a tensile load when the device is in normal use. Moreover, the torque required to rotate the rod is sometimes substantial, which places substantial forces on the point of connection between the threaded rod and the driver. As a result of these loads, together with potential bending moments and eccentric loading, stresses are localized at the junction of the threaded rod and the driver when such a device is loaded.

While currently-available bone adjustment systems have produced excellent results, many of these devices exhibit one or more shortcomings or disadvantages that render the device susceptible to failure. For example, a problem has been encountered where the stress concentrations at the point where the threaded rod is affixed to the driver can cause failure of the device at this junction. Failures of a device at this junction results in the inability of the device to perform its intended bone adjustment action. For these reasons among others, a need remains for further improvements in this technological field. The present disclosure addresses this need.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present disclosure provides implantable reconfigurable bone adjustment devices, kits, systems and methods for moving first and second members of the device, and hence first and second bone segments, portions or fragments coupled thereto, with respect to one another.

There is provided a reconfigurable bone adjustment device including a first member configured for attachment to a first bone fragment, a second member configured for attachment to a second bone fragment, and a reconfiguration assembly configured to move the second member relative to the first member. The reconfiguration assembly including a drive mechanism including a driver, the drive mechanism operable to controllably rotate the driver, and a threaded rod having a proximal end operatively coupled to the driver at a junction so that rotation of the drive mechanism rotates the driver, which rotates the threaded rod. The reconfigurable bone adjustment device further including means for reducing applied stresses at the junction.

In some embodiments, the driver has a first axis of rotation and the threaded rod has a second axis of rotation, the first and second axes of rotation being offset with respect to one another.

In some embodiments, the threaded rod includes a helical channel formed therein, the helical channel being formed in a proximal portion of the threaded rod adjacent to the proximal end of the threaded rod adjacent to the junction.

In some embodiments, the junction includes a dynamic joint selected from one of a pin joint, a ball joint, or a universal joint for connecting the proximal end of the threaded rod to the driver.

In some embodiments, the driver includes first and second projections having first and second apertures, respectively, the first and second projections being configured to receive the proximal end of the threaded rod therebetween, the threaded rod including an aperture near the proximal end thereof so that, when aligned, a pin is inserted through the first and second projections of the driver and the aperture of the threaded rod to secure the threaded rod to the driver.

In some embodiments, the reconfigurable bone adjustment device includes a collar positioned between the driver and the second member such that rotation of the threaded rod in a first direction exerts a compressive force between a distal surface of the driver and a proximal surface of the collar, and between a distal surface of the collar and a proximal end of the second member.

In some embodiments, the distal surface of the collar includes a convex surface for contacting a complementary concave surface formed on the proximal end of the second member, the complementary convex and concave surfaces forming an interface for transmitting the compressive force.

In some embodiments, the threaded rod includes a first distal segment having a first diameter and a second proximal segment adjacent the proximal end of the threaded rod, the second proximal segment having a second diameter, the second diameter being greater than the first diameter.

In some embodiments, the second proximal segment includes a tapered surface extending from the proximal end of the threaded rod to the first distal segment, rotation of the threaded rod causes the tapered surface of the second proximal segment to contact a proximal end of the second member.

In some embodiments, the threaded rod includes a third segment having a third diameter, the third diameter being greater than the first diameter and the second diameter.

In some embodiments, the third segment is located in-between the first and second segments.

In some embodiments, the third segment includes an enlarged spherical segment.

In some embodiments, the enlarged spherical segment includes an articulating surface for contacting a proximal end of the second member.

In some embodiments, the articulating surface of the enlarged spherical segment and the proximal end of the second member include corresponding concave and convex articulating surfaces.

In some embodiments, the articulating surface of the enlarged spherical segment and the proximal end of the second member include corresponding spherical articulating surfaces.

In some embodiments, the driver is operatively coupled to a proximal end of the second member via a ball joint type connection.

In some embodiments, the junction includes a stop component coupled to the threaded rod adjacent to the proximal end of the threaded rod and a spacer component. The spacer component including (i) a bore dimensioned to permit passage of the threaded rod therethrough, (ii) a distal surface configured to contact a proximal end of the second member, and (iii) a cavity extending from a proximal side of the spacer component, the cavity dimensioned to receive the stop component therein.

In some embodiments, the cavity formed in the spacer component and the stop component have complementary surfaces so that rotation of the spacer component rotates the stop component.

In some embodiments, the stop component includes a body having an aperture and the threaded rod includes an aperture, the aperture formed in the body and the aperture formed in the threaded rod being aligned with one another for receiving a pin therethrough. The pin includes a first end, a second end, and a length defined by the first and second ends, the length of the pin being greater than an outer dimension of the body so that the first and second ends of the pin extend beyond the body of the stop component. The spacer component including a channel for receiving the first and second ends of the pin when the stop component is received within the cavity of the spacer component, wherein the first and second ends of the pin contact one or more side surfaces of the channel when the driver is rotated so that torque is transferred from the spacer component to the threaded rod.

In some embodiments, the stop component includes a radially extending flange, the cavity formed in the spacer component including a shoulder dimensioned to contact the flange when the stop component is received within the cavity.

In some embodiments, the stop component includes a distal side having a geometric shape defined by a plurality of distal contact surfaces, and the cavity formed in the proximal side of the spacer component includes a plurality of complementary contact surfaces so that, when the stop component is received within the cavity, the contact surfaces of the cavity contact the distal surfaces of the stop component.

In some embodiments, the junction includes a welded joint between the proximal end of the threaded rod and the driver.

In some embodiments, the reconfigurable bone adjustment device is an intramedullary limb lengthening nail.

In some embodiments, the reconfigurable bone adjustment device is an intramedullary bone transport nail.

In some embodiments, the drive mechanism is an internal magnetic adapted for rotation via an external magnetic actuator.

Embodiments of the present disclosure provide numerous advantages. For example, incorporation of the reconfiguration assembly operates to reduce applied stresses, such as axial forces, torsional forces, bending moments and/or eccentric moments on the junction and/or by configuring the junction in a manner whereby one of more of the forces, torsional forces, bending moments and/or eccentric moments is isolated away from the junction.

Further features and advantages of at least some of the embodiments of the present disclosure, as well as the structure and operation of various embodiments of the present disclosure, are described in detail below with reference to the accompanying drawings.

BRIEF DESCRIPTION OF THE FIGURES

FIG. 3 illustrates a side view of an example embodiment of an intramedullary limb lengthening nail that may incorporate a reconfiguration assembly such as that show in FIG. 2, the limb lengthening nail illustrated in a retracted or contracted state;

FIG. 4 illustrates a side view of the intramedullary limb lengthening nail shown in FIG. 3, the limb lengthening nail illustrated in an extended or distracted state;

FIG. 5 illustrates a cross-sectional view of the limb lengthening nail shown in FIG. 4, taken along line 5-5;

FIG. 6 illustrates a side view of an example embodiment of an intramedullary bone transport nail that may incorporate a reconfiguration assembly such as that show in FIG. 2, the intramedullary bone transport nail shown with a transport carriage assembly located at a first position;

FIG. 7 illustrates a side view of the intramedullary bone transport nail show in FIG. 6, the intramedullary bone transport nail shown with a transport carriage assembly located at a second position;

Figure 1:
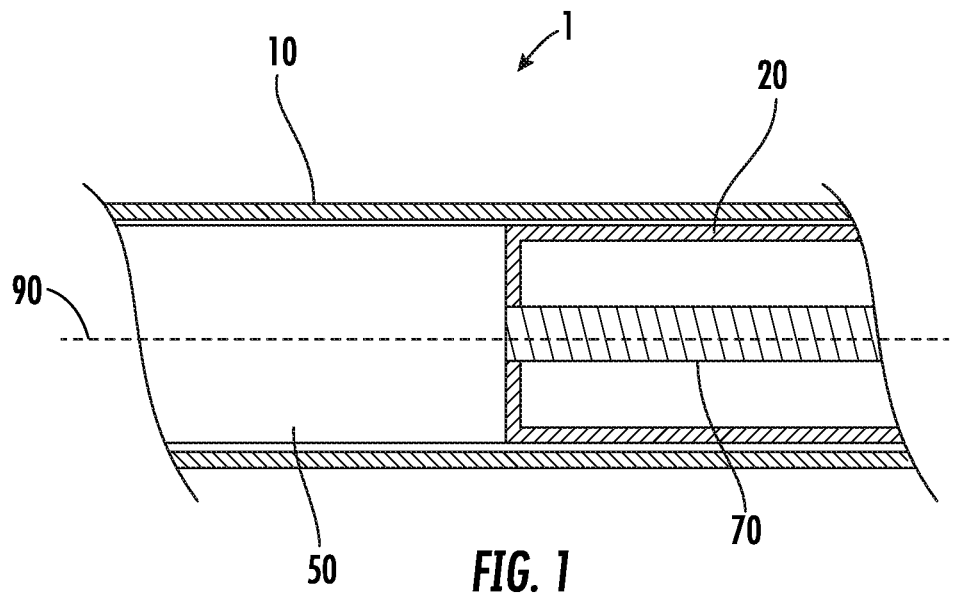
FIG. 1 illustrates a partial schematic representation, in partial cross section, of an example embodiment of an implantable reconfigurable bone adjustment device.
Figure 2:
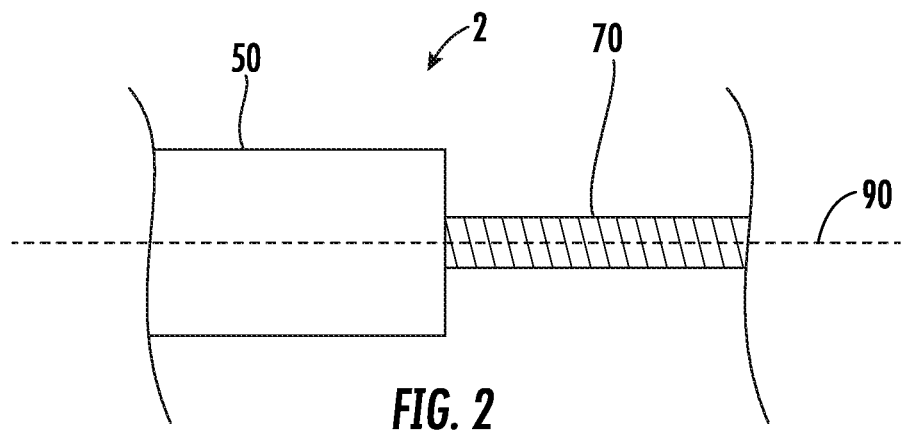
FIG. 2 illustrates a partial schematic representation of an example embodiment of a reconfiguration assembly used in connection with the implantable reconfigurable bone adjustment device shown in FIG. 1.
Figure 8:
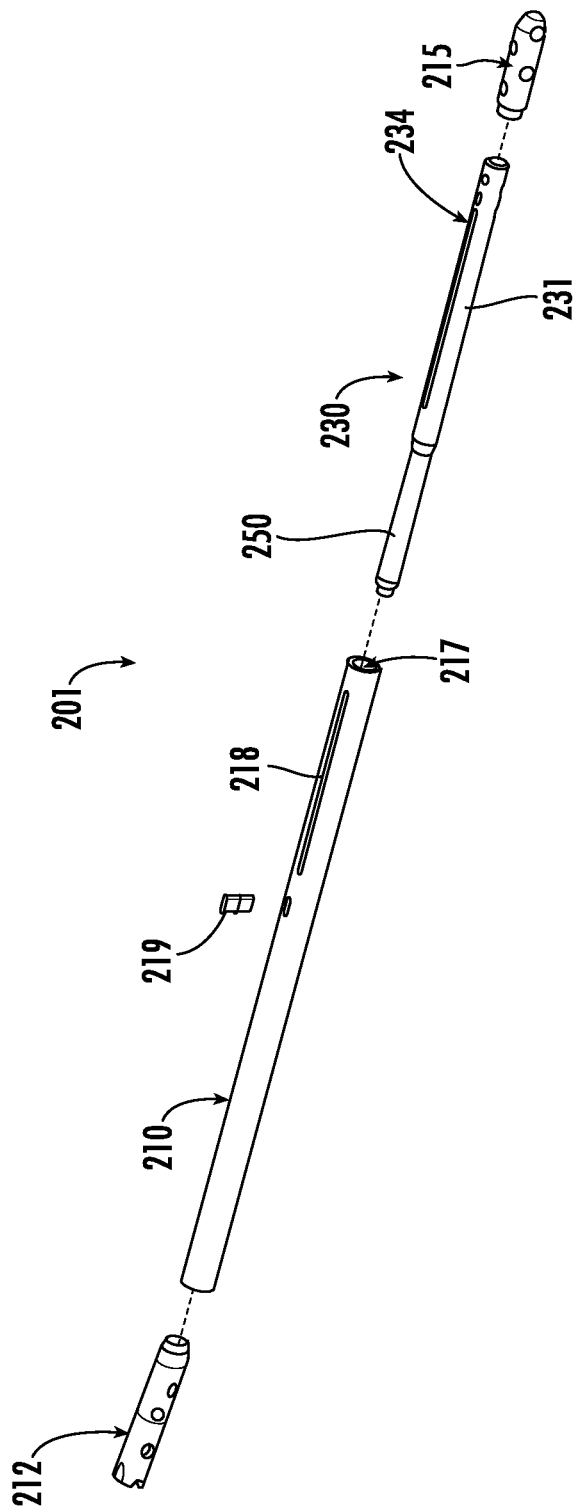
FIG. 8 illustrates an exploded perspective view of the intramedullary bone transport nail shown in FIGS. 6 and 7.
Figure 9:
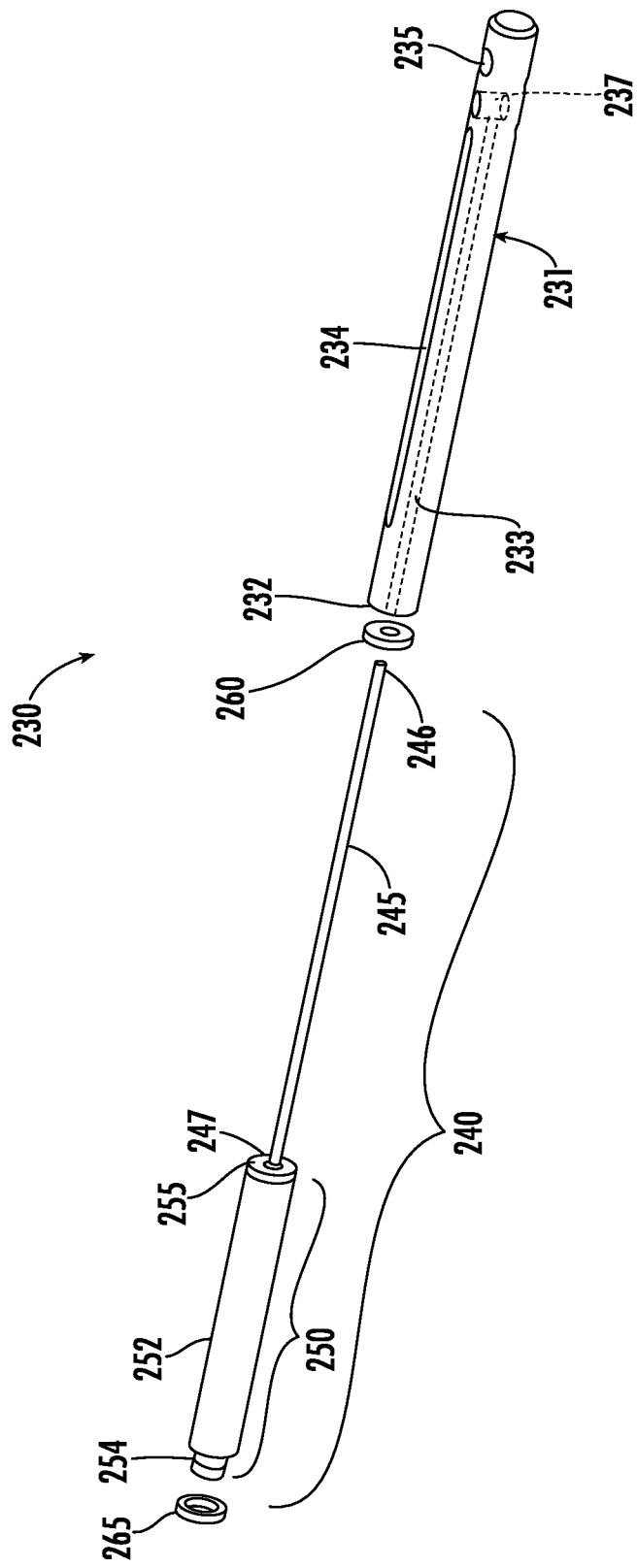
FIG. 9 illustrates an exploded perspective view of an example embodiment of a carriage assembly used in connection with the bone transport nail shown in FIGS. 6-8.

It should be understood that the drawings are not necessarily to scale and that the disclosed embodiments are sometimes illustrated diagrammatically and in partial views. In certain instances, details which are not necessary for an understanding of the disclosed methods and devices or which render other details difficult to perceive may have been omitted. It should be further understood that this disclosure is not limited to the particular embodiments illustrated herein.

DETAILED DESCRIPTION

For the purposes of promoting an understanding of the principles of the present disclosure, reference will now be made to the embodiments illustrated in the figures and specific language will be used to describe the same. It will nevertheless be understood that no limitation of the scope of the disclosure is thereby intended. Any alterations and further modifications in the described embodiments, and any further applications of the principles of the present disclosure as described herein are contemplated as would normally occur to one skilled in the art to which the disclosure relates.

Various implantable reconfigurable bone adjustment devices are disclosed herein. In one embodiment, the implantable reconfigurable bone adjustment device may include a first member, body portion or component (used interchangeably herein without the intent to limit), a second member, and a rotatable threaded rod that engages at least one component affixed to the first member and at least one component operable to axially move the second member relative to the first member. The implantable reconfigurable bone adjustment device may also include a drive mechanism to controllably actuate rotation of the threaded rod. In certain embodiments, the drive mechanism may be an internal magnet coupled to the threaded rod such that rotation of the internal magnet drives rotation of the threaded rod. This can be achieved, for example, by fixing the threaded rod directly to the internal magnet or a casing in which the internal magnet is contained, or can be achieved by connecting the threaded rod indirectly to the internal magnet, such as through a gear mechanism or other structure positioned therebetween. As described further herein, torque may be applied to the internal magnet by applying a rotating magnetic field across the internal magnet from an external source. In other implantable reconfigurable bone adjustment device embodiments, rotation of the threaded rod may be controlled or driven by a drive mechanism other than an internal magnet. Alternative drive mechanisms for driving the threaded rod may include any other now known or hereafter developed drive mechanisms known to a person of ordinary skill in the art, including, for example, an electric motor with or without gear reducer, a current source inside or outside the patient's body, a permanent magnet with a gear reducer and a rotating magnetic field source external to the patient, etc. In alternate embodiments, the drive mechanism can be configured to drive the threaded rod in one direction only, or in both directions, according to requirements.

The first and second body portions are dimensioned such that the body portions can move in at least one axial direction with respect to one another upon rotation of the threaded rod. In one representative embodiment, depicted schematically in FIG. 1, the implantable reconfigurable bone adjustment device 1 may include a first body 10 and a second body 20 at least partially received within first body 10. The first body 10 may also house a reconfiguration assembly 2 which, in this embodiment, includes an internal magnet 50, which is affixed to a threaded rod 70. As described in further detail below, the internal magnet 50 may be rotated about an axis 90 of the device 1 by application of an external rotating magnetic field, which may be applied, for example, using an external magnetic actuator, as discussed further below.

One representative, but non-limiting, example of an implantable reconfigurable bone adjustment device contemplated by the present disclosure is an intramedullary limb lengthening nail, such as intramedullary ("IM") limb lengthening nail 101 depicted in FIGS. 3-5. Further details regarding representative IM limb lengthening nails are available in U.S. Pat. No. 8,777,947, which is hereby incorporated herein by reference in its entirety. Referring to FIGS. 3-5, the IM limb lengthening nail 101 may include a proximal body portion 110, a distal body portion 130, and a threaded rod 170 operatively associated with the proximal body portion 110 and the distal body portion 130. In use, rotation of the threaded rod 170 causes the proximal body portion 110 and the distal body portion 130 to move with respect to one another. In one embodiment, as will be described in greater detail, the proximal body portion 110 may be configured as an outer body and the distal body portion 130 may be configured as an inner body so that at least a portion of the distal body portion 130 may be received with the proximal body portion. Alternatively, it is envisioned that the proximal body portion may be configured as the inner body and the distal body portion may be configured as the outer body. In one embodiment, the threaded rod 170 may be mounted in and coupled to the distal body portion 130.

Each of the proximal body portion 110, distal body portion 130, and threaded rod 170 has a proximal end 111, 131, 171 and a distal end 114, 134, 174, respectively. The IM limb lengthening nail 101 may also include a reconfiguration assembly 102, which may include an inner magnet 150 (also referred to herein as "internal magnet") seated in the proximal body portion 110 and coupled to the proximal end 171 of the threaded rod 170, a distal block 136 coupled to the distal body portion 130 and a distal end 174 of the threaded rod 170, and a threaded block 119 coupled to the proximal body portion 110 and engaged with the threaded rod 170. The term "inner" or "internal" is used herein in reference to the magnet 150 to distinguish this magnet from a different magnet or multiple different magnets employed by an external actuator as described in greater detail below, which magnet or magnets of an external actuator, are referred to as "outer magnets." While neodymium magnets are suggested, other magnets may be employed as will be apparent to those skilled in the art.

The proximal body portion 110 may be at least partially hollow, having an inner wall 120 that defines an internal cylindrical chamber, for accommodating a portion of the distal body portion 130, which extends through the distal end 114 of the proximal body portion 110. The proximal and distal body portions 110, 130 are dimensioned such that the proximal and distal body portions 110, 130 can move in both axial directions with respect to one another. The proximal body portion 110 may also house the inner magnet 150, which may be mounted in a casing or carrier to facilitate the coupling of the inner magnet 150 to the threaded rod 170. The inner magnet 150 may include at least one permanent magnet, one of the poles of which is directed in one radial direction relative to a longitudinal axis 190 of the IM limb lengthening nail 101 and the other pole directed in an opposite radial direction relative to the longitudinal axis 190. As described in further detail below, the inner magnet 150 may be rotated about the longitudinal axis 190 of the IM limb lengthening nail 101 by application of an externally applied rotating magnetic field. The IM limb lengthening nail 101 may also include a first locking portion 112 and a second locking portion 132, each of which includes a plurality of fastener openings 113, 133 structured to receive fasteners for coupling the respective ends of the IM limb lengthening nail 101 to the patient's bone.

The inner magnet 150 is coupled to the threaded rod 170, which extends through the proximal end 131 of the distal body portion 130. The threaded rod 170 may also extend through a bearing (not shown) which engages the inner wall 120 of the proximal body portion 110. Similarly, a bearing may be coupled to a proximal end of the inner magnet 150 to facilitate rotation of the inner magnet 150 within the proximal body portion 110. The distal end 174 of the threaded rod 170 is engaged with the distal block 136, which is coupled to the distal body portion 130. In use, the distal block 136 permits rotation of the threaded rod 170 with respect to the distal body portion 130, and couples the distal body portion 130 and the threaded rod 170 for joint movement along the longitudinal axis 190. For example, the distal block 136 may be coupled or affixed to the distal body portion 130 such that the threaded rod 170 can rotate freely without altering the position of the distal end 174 of the threaded rod 170 with respect to the distal body portion 130. The threaded rod 170 also extends through the threaded block 119, which is coupled to the proximal body portion 110.

The threaded rod 170 may include a set of external threads 176 which are engaged with a set of internal threads formed in a threaded bore (not shown) of the threaded block 119. As noted above, the threaded rod 170 is axially coupled to the distal body portion 130 and is axially and rotationally coupled to the inner magnet 150, and the threaded block 119 is engaged with the threaded rod 170 and axially and rotationally coupled to the proximal body portion 110. As a result, rotation of the inner magnet 150 causes relative movement of the proximal and distal body portions 110, 130 along the longitudinal axis 190.

FIG. 3 illustrates the IM limb lengthening nail 101 in a retracted or contracted state, and FIGS. 4 and 5 illustrate the IM limb lengthening nail 101 in an extended or distracted state. The IM limb lengthening nail 101 may be moved between the contracted and distracted states by rotating the inner magnet 150 by application of an externally applied rotating magnetic field. More specifically, rotation of the inner magnet 150 may cause rotation of the threaded rod 170 and movement of the threaded block 119 and the proximal body portion 110 relative to the distal body portion 130 along the longitudinal axis 190, thereby adjusting the length of the IM limb lengthening nail 101. As is evident from a comparison of FIGS. 3 and 4, the longitudinal positions of the distal block 136 and the distal end 174 of the threaded rod 170 with respect to the distal body portion 130 remain unchanged. That is, the distal body portion 130 may include an elongated slot 140 which enables the threaded block 119 to slide along the distal body portion 130 during relative movement of the proximal and distal body portions 110, 130 along the longitudinal axis 190.

In use, the IM limb lengthening nail 101 is configured for implantation in a bone having a medullary canal. Typically, the IM limb lengthening nail is implanted such that the first locking portion 112 is affixed to a first bone portion and the second locking portion 132 is affixed to a second bone portion, and a gap separates the first and second bone portions. The gap may be formed, for example, during an osteotomy procedure in which the bone is severed for purposes of lengthening the bone over time. The IM limb lengthening nail 101 is implanted into the medullary canal of the bone and is surgically coupled to the bone. For example, the proximal body portion 110 is coupled to the first bone portion and the distal body portion 130 is coupled to the second bone portion by fasteners such as screws or pins, which may be received in or otherwise engaged with the openings 113, 133.

Both distraction and compaction of the proximal and distal body portions 110, 130 with respect to each other is possible. Thus, with the IM limb lengthening nail 101 implanted in the bone, the segmented portions of the bone may be distracted or compacted as necessary by rotation of the threaded rod 170 and the inner magnet 150 in a first direction or a second direction, respectively, thereby enabling lengthening or shortening of the bone. In other words, the telescoping ability allows the IM limb lengthening nail 101 to both distract and contract the bone portions, to which the proximal and distal body portions 110, 130 are coupled. During lengthening, the IM limb lengthening nail 101 may be transitioned from the retracted state (FIG. 3) to the expanded state (FIG. 4), thereby lengthening the bone. The IM limb lengthening nail may be transitioned from the retracted state to the expanded state gradually over a given period of time, such that an ossified region forms as the bone lengthens and heals. It should be understood that the principles and features of the present disclosure are not limited to use with the IM limb lengthening nail illustrated and described in connection with FIGS. 3-5 and that the principles and features may be used in combination with other IM limb lengthening nails.

In another embodiment, an implantable reconfigurable bone adjustment device contemplated by the present disclosure is an IM bone transport nail, such as the IM bone transport nail 201 depicted in FIGS. 6-9. IM bone transport nails typically are employed in situations where regeneration of bone across a gap between two bone fragments is indicated. For example, typically a gap of 3 cm or more may be formed such as, for example, as a result of a surgical resection. In an example bone transport procedure, two bone fragments, a distal end fragment and a proximal end fragment, are held in a displaced relationship to each other by, for example, a medullary pin or nail fixed in the medullary canal of each bone fragment. A middle bone segment, which also originates from the same original bone tissue as the two bone fragments, is positioned adjacent a first one of the two bone fragments. At a contact site between the middle bone segment and the first one of the end bone fragments, bone tissue grows as a result of normal physiological bone healing processes. Regenerate bone thereafter continues to form in a longitudinal direction relative to the medullary canal by displacement of the middle bone segment toward the second one of the two bone fragments at a prescribed rate of translation of the middle segment, i.e., a rate that is sufficiently slow to allow bone regeneration to take place.

Referring to FIGS. 6-9, the IM bone transport nail 201 may include a proximal locking portion 212 configured for fixation to a first bone fragment 295, a distal locking portion 215 configured for fixation to a second bone fragment 296, and a nail body 210 extending between the proximal locking portion 212 and the distal locking portion 215. The IM bone transport nail 201 is configured for use, for example, where the gap in which bone is to be regenerated is located in a proximal femoral or distal tibial location. Each of proximal locking portion 212 and distal locking portion 215 may include a plurality of fastener openings positioned roughly perpendicular to a longitudinal axis 290 of IM bone transport nail 201 and structured to receive fasteners, also referred to as fixation elements, such as, for example, locking screws or bolts (not shown) for anchoring each of the proximal locking portion 212 and distal locking portion 215 to respective first and second bone fragments of a patient. In the embodiment shown, proximal and distal locking portions 212, 215 define first openings 213 and second openings 216, respectively.

The nail body 210 of the IM bone transport nail 201 may be roughly cylindrical and may include at least a partially hollow cavity to accommodate a transport carriage assembly 230. For example, the nail body 210 may include an internal chamber 217 configured to receive and retain the transport carriage assembly 230 in an axially slidable arrangement. The internal chamber 217 of the nail body 210 and the transport carriage assembly 230 are dimensioned such that the transport carriage assembly 230 can translate axially within the nail body 210. That is, the nail body 210 may include an elongated longitudinal opening or slot 218 that opens diametrically out on opposite sides of the nail body 210 at an axial position corresponding to the axial range of motion desired for movement of a transport bone segment screw 236 that is affixed to a middle bone segment 297 during normal use of the IM bone transport nail 201. That is, the middle bone segment 297 is situated between a first bone fragment 295, which typically is a first end of a long bone, and a second bone fragment 296, which typically is a second end of a long bone. Movement of the middle bone segment 297 from its initial position shown in FIG. 6 to its final position shown in FIG. 7 produces regenerate bone 298 between the first bone fragment 295 and the middle bone segment 297. In alternate embodiments, the first bone fragment 295 can be a proximal bone fragment or a distal bone fragment. For example, the IM bone transport nail 201 is well suited for a bone transport procedure to regenerate bone for repair of a proximal femoral or distal tibial defect. When the IM bone transport nail 201 is used for repair of a proximal femoral defect, the first bone fragment 295 is a distal end fragment of a femur and the second bone fragment 296 is a proximal end fragment of the femur. When the IM bone transport nail 201 is used for repair of a distal tibial defect, the first bone fragment 295 is a proximal end fragment of a tibia and the second bone fragment 296 is a distal end fragment of the tibia.

The transport carriage assembly 230 may include a carriage body 231, a threaded rod 245 and a magnetic driver 250. The threaded rod 245 may be coupled to the magnetic driver 250 in axial alignment. Together, the threaded rod 245, the magnetic driver 250 and their respective components are referred to in this embodiment as a "magnet housing assembly." The magnetic driver 250 includes an inner magnet 251, which may be accommodated in a casing or carrier to facilitate coupling of the inner magnet 251 to the threaded rod 245. In one embodiment, the inner magnet 251 is hermetically sealed in a housing as described further below. The term "inner" is used herein in reference to the magnet of the magnetic driver 250 to distinguish this magnet from a different magnet or multiple different magnets employed by an external actuator as described in greater detail below, which magnet or magnets of an external actuator, are referred to as "outer magnets." The magnet housing assembly of the embodiment shown includes the inner magnet 251, a magnet housing 252, a first magnet housing cap 254 and a second magnet housing cap 255. In the embodiment shown, the inner magnet 251, the magnet housing 252, the first magnet housing cap 254, the second magnet housing cap 255 and the threaded rod 245 are assembled and coupled together such that rotation of the inner magnet 251 rotates the remaining elements. In one manner of assembly, for example, these components are welded together to achieve rotation of these elements together. In one embodiment, the inner magnet 251 is hermetically sealed within the magnet housing 252, which prevents contact of the inner magnet 251 with the patient's body. As shown, the carriage body 231 and the magnet housing 252 may be roughly cylindrical in this embodiment and have outer diameters that are roughly equal to the inner diameter of the internal chamber 217 of the nail body 210. In the embodiment shown, the inner magnet 251 includes a permanent magnet with diametrical magnetization. In other words, the poles of the inner magnet 251 are perpendicular to the rotational axis of the internal magnet 251. While neodymium magnets are suggested, other magnets may be employed as will be apparent to those skilled in the art.

The Carriage body 231 of the transport carriage assembly 230 may include a radially oriented aperture 235 in which a transport bone segment screw 236 is positionable during use of the IM transport nail 201. In use, the transport bone segment screw 236 fixes the middle bone segment 297 to the carriage body 231. The carriage body 231 may also include an axial bore 233 and an elongated longitudinal opening or slot 234.

The axial bore 233 is configured to accommodate or receive at least a portion of the threaded rod 245 within the carriage body 231 without restricting free rotation of the threaded rod 245 relative to the carriage body 231. The axial bore 233 therefore may include a radial dimension greater than the largest diameter of the threaded rod 245 and an axial dimension sufficient to accommodate the full length of the threaded rod 245 when the transport carriage assembly 230 is fully assembled for use. Upon assembly of the transport carriage assembly 230 by insertion of the threaded rod 245 into the axial bore 233, a bearing ring 260 may be positioned between the second magnet housing cap 255 and the proximal end 232 of carriage body 231 to reduce frictional forces of the assembly and enable the magnet housing assembly 240 to rotate freely within the nail body 210 relative to the carriage body 231. The magnet housing assembly 240 in the embodiment shown also includes an optional bearing ring 265 adjacent to the first magnet housing cap 254 to facilitate rotation of the magnetic driver 250 within the nail body 210. For example, incorporation of the optional bearing ring 265 may operate to reduce frictional forces within the IM bone transport nail 201 should the proximal end of the magnet housing assembly 240 come into contact with other surfaces within the internal chamber 217.

The elongated slot 234 formed in the carriage body 231 may be configured to accommodate a threaded block 219, and to provide clearance relative to the threaded block 219 when the transport carriage assembly 230 moves axially relative to the nail body 210 (to which the threaded block 219 is affixed) during normal operation of the IM bone transport nail 201 following implantation into a patient. While the elongated slot 234 in this embodiment passes entirely through the carriage body 231, which enables the threaded block 219 to extend diametrically to both opposing sides of the nail body 210, in alternative embodiments (not shown) the elongated slot 234 can be formed as a groove on one side of the carriage body 231 that extends only part way through the carriage body 231 and opens radially out on only one side of the carriage body 231. In this alternate embodiment, the threaded block 219 may be affixed to the nail body 210 only on one side of the nail body 210.

The magnetic driver 250 in this embodiment may be rigidly coupled to the proximal end 247 of the threaded rod 245. In this embodiment, the magnetic driver 250 and the threaded rod 245 are rotationally fixed relative to one another. Fixation of the magnetic driver 250 to the threaded rod 245 can be achieved by any mechanism now known or hereafter developed including, for example, welding the proximal end 247 of the threaded rod 245 to the second magnet housing cap 255, which is in turn welded to the distal end of the magnet housing 252. In this embodiment, welding of the threaded rod 245 to the magnetic driver 250 eliminates any degrees of rotational freedom between the threaded rod 245 and the magnetic driver 250. Therefore, axial rotation of the magnetic driver 250 directly drives axial rotation of the threaded rod 245. Other embodiments are contemplated, however, where components comprising gears or other mechanisms are incorporated into the transport carriage assembly 230 between the inner magnet 251 and the threaded rod 245 to modify the relative rate of rotation between these two components. This may be desired, for example, to increase torque applied to the threaded rod 245 or for other reasons. In such embodiments, rotation of the inner magnet 251 drives rotation of the threaded rod 245.

The threaded rod 245, at a location between the proximal end 247 of the threaded rod 245 that is coupled to the magnetic driver 250 and the distal end 246 of the threaded rod 245 that may be accommodated within the access slot 237, engages the threaded block 219. The threaded block 219 may include a threaded bore (not shown) extending through the threaded block 219 along the longitudinal axis 290. The threaded rod 245 includes a set of external threads that are engaged with a set of internal threads formed in the threaded bore of the threaded block 219. Stated alternatively, the external threads of the threaded rod 245 include diameter and pitch features complementary to those of the internal threads of the threaded bore such that outward facing threads on the threaded rod 245 properly engage inward facing threads in the threaded bore of the threaded block 219. The threaded block 219 may be fixed to the nail body 210 so that the position of the threaded block 219 is fixed with respect to the nail body 210. The threaded block 219 permits rotation of the threaded rod 245 relative to the nail body 210, and rotatably couples the nail body 210 and the threaded rod 245 to drive axial movement of the transport carriage assembly 230 along the longitudinal axis 290. In the embodiment shown, the threaded block 219 is coupled to diametrically opposite sides of the nail body 210 in an orientation whereby the threaded block 219 passes through the elongated slot 234 of the carriage body 231, which is positioned within the internal chamber 217 of the nail body 210. In this orientation, rotation of the magnetic driver 250 results in rotation of the threaded rod 245 within the threaded bore of the threaded block 219 and, because the threaded block 219 is fixed to the nail body 210, rotation of the magnetic driver 250 and the threaded rod 245 results in axial movement of the transport carriage assembly 230 relative to the nail body 210 along the longitudinal axis 290 of the IM bone transport nail 201.

FIG. 6 illustrates the IM bone transport nail 201 with the transport carriage assembly 230 located at a first position, and FIG. 7 illustrates the IM bone transport nail 201 with transport carriage assembly 230 located at a second position. The transport carriage assembly 230 may be moved between the first and second positions by rotating the inner magnet 251 with an externally actuated rotating magnetic field, as described more fully below. In use, rotation of the inner magnet 251 causes rotation of the threaded rod 245 and movement of the transport carriage assembly 230 along the longitudinal axis 290, thereby axially adjusting the position of the transport carriage assembly 230 within the IM bone transport nail 201. As is evident from a comparison of FIGS. 6 and 7, the axial position of the threaded block 219 with respect to the nail body 210 remains unchanged and the axial positions of the magnetic driver 250, the threaded rod 245 and the carriage body 231 translate relative to the nail body 210, but remain unchanged relative to one another. The elongated longitudinal opening 218 of the nail body 210 enables the transport carriage assembly 230 to move axially relative to the nail body 210 with the transport bone segment screw 236 affixed to the middle bone segment 297 passing through the elongated longitudinal opening 218.

Displacement of the transport carriage assembly 230 as described above is achieved by rotation of the threaded rod 245, which may be achieved by rotation of the inner magnet 251. In the IM bone transport nail 201, the threaded rod 245 is under tension during axial loading conditions resulting from rotation of the threaded rod 245. More specifically, during rotation of the threaded rod 245 and displacement of the transport carriage assembly 230, the load-bearing points of contact between the nail body 210 and the magnetic driver 250 are at (i) the threaded rod 245/threaded block 219 interface, (ii) the abutment of the proximal end of the carriage body 231 with the second magnet housing cap 255 (through bearing 260), and (iii) at the junction between the threaded rod 245 and the second magnet housing cap 255.

For example, when the transport carriage assembly 230 is moved in a direction represented by the arrow on FIG. 6 as a result of rotation of the threaded rod 245, the transport bone segment screw 236 transmits a tensile force on the transport bone segment 297 to which the transport bone segment screw 236 is affixed, relative to the first bone fragment 295. The transport bone segment screw 236 thereby exerts a compressive load on the carriage body 231 via the engagement of the transport bone segment screw 236 in radially oriented aperture 235. This compressive force is transmitted by the carriage body 231 to the second magnet housing cap 255, thereby causing tension in the portion of the threaded rod 245 that extends from the second magnet housing cap 255 to the threaded block 219, which is fixed to the nail body 210. Thus, the axial load on the threaded rod 245 is between the threaded block 219 (affixed to the nail body 210) and the proximal end 247 of the threaded rod 245 at its junction with the second magnet housing cap 255. When the IM bone transport nail 201 is under a compressive axial load, which it is during use, the axial load on the threaded rod 245 is tensile. In other words, when the transport carriage assembly 230 is under compression, it imparts this load to the magnetic driver 250, for example, the second magnet housing cap 255, which in turn puts a tensile load on the threaded rod 245 between the second magnet housing cap 255 (where it is coupled) and where it is threaded into the locking block 219. As the carriage distracts, the length of the threaded rod 245 under load decreases.

Rotation of the threaded rod 245 is achieved by applying a rotational force on the inner magnet 251 that overcomes opposing forces to rotate the inner magnet 251. Because the inner magnet 251 is fixedly contained within the magnet housing 252 and the second magnet housing cap 255 is fixedly coupled to the magnet housing 252 and the threaded rod 245, rotation of the inner magnet 251 drives rotation of the threaded rod 245. Rotation of the inner magnet 251 is achieved by applying an appropriately positioned and oriented rotating magnetic field (also referred to herein as a magnetic driving field) of sufficient strength across the inner magnet 251.

It should be understood that the principles and features of the present disclosure are not limited to use with the IM bone transport nail illustrated and described in connection with FIGS. 6-9 and that the principles and features may be used in combination with other IM bone transport nails. In addition, while the IM limb lengthening nail 101 and IM bone transport nail 201 are described as representative implantable reconfigurable bone adjustment devices, it is to be understood that the present disclosure in not limited to use with an IM limb lengthening nail or an IM bone transport nail, it being understood that the principles and features of the present disclosure find advantageous use with a variety of other implantable reconfigurable bone adjustment devices that include a drive mechanism operable to controllably rotate a driver that is coupled to a threaded rod to drive rotation of the threaded rod to move first and second members of the device relative to one another.

As indicated above, to rotate the rotatable portion of an implanted medical device that employs a drive mechanism including an internal magnet, such as, for example, a rotatable internal magnet 50, 150, 251 that is coupled to a threaded rod 70, 170 and 245 of the devices described above, a rotating magnetic field is applied to the device to apply torque to the internal magnet. In one embodiment, this torque is applied by magnetically coupling an external magnetic actuator with the rotatable internal magnet 50, 150, 251.

The creation of a magnetic driving field for rotating internal magnets 50, 150, 251 and threaded rods 70, 170, 245 coupled coaxially therewith can be accomplished by a wide variety of mechanism. In one manner of actuating rotation of internal magnets 50, 150, 251 following implantation of an implantable reconfigurable bone adjustment device 1, 101, 201 in a skeletal position of a patient, an external magnetic actuator, also referred to herein as an actuation unit may be used. In one embodiment, the external magnetic actuator is operable to position a driving magnet, also referred to herein as an outer magnet, near the implanted device, but external to the patient, at the height of the internal magnet 50, 150, 251. The external magnetic actuators are designed and positioned to maximize torque to the internal magnets 50, 150, 251 and the threaded rod 70, 170, 245 and, in any event, to provide sufficient torque to rotate the internal magnets 50, 150, 251 despite the distance between the internal magnets 50, 150, 251 and the one or more outer magnets in the external magnetic actuator and applied resisting forces on the device 1, 101, 201. In this regard, rotation of the internal magnet 50, 150, 251 must overcome any compressive load imparted between the components of the device 1, 101, 201 by bone tissue and other tissues of the patient, together with internal frictional forces of the device.

In the presence of a magnetic driving field perpendicular to the rotational axis of the internal magnet 50, 150, 251 (which lies on the longitudinal axis 90, 190, 290 in the respective embodiments) and rotating around this axis, the internal magnet 50, 150, 251 tends to become oriented in the magnetic driving field, which applies a torque to the internal magnet 50, 150, 251 and causes the internal magnet 50, 150, 251 to rotate in the same rotational direction of the magnetic driving field, together with threaded rod 70, 170, 245 that is coupled coaxially with internal magnet 50, 150, 251, if the applied torque is greater than the load torque on threaded rod 70, 170, 245 under the load applied to it at the time when the magnetic driving field is activated.

In one embodiment, the driving magnet comprises at least one permanent magnet, one of the poles of which is directed towards longitudinal axis 90, 190, 290. In another embodiment, an even greater torque can be applied to the internal magnet 50, 150, 251 by using two permanent driving magnets positioned such that the south pole of one is facing the north pole of the other, and such that the implanted device and the part of the patient's body that surrounds the implanted device are positioned between the two permanent magnets.

Figure 23:
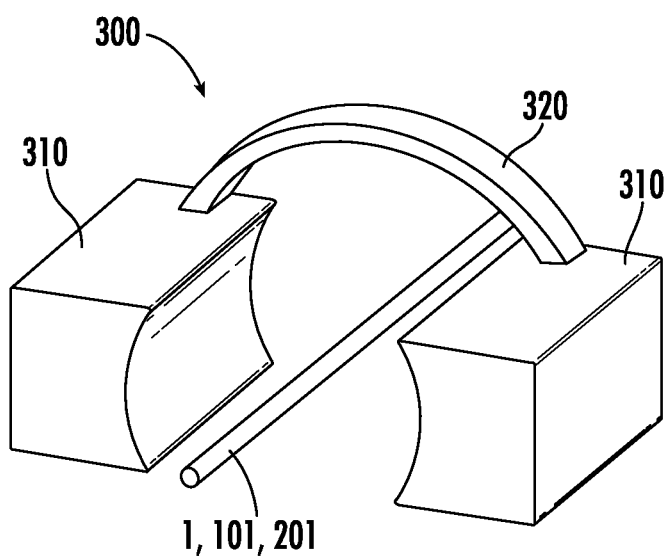
FIG. 23 illustrates a perspective view of a system according to an example embodiment that includes an implantable reconfigurable bone adjustment device and an actuating mechanism.
Figure 24:
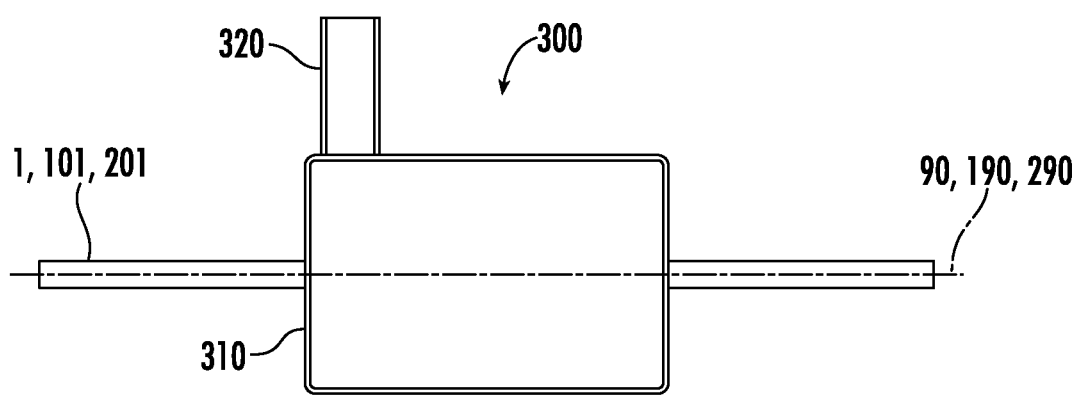
FIG. 24 illustrates a side view of the system shown in FIG. 23.
Figure 25:
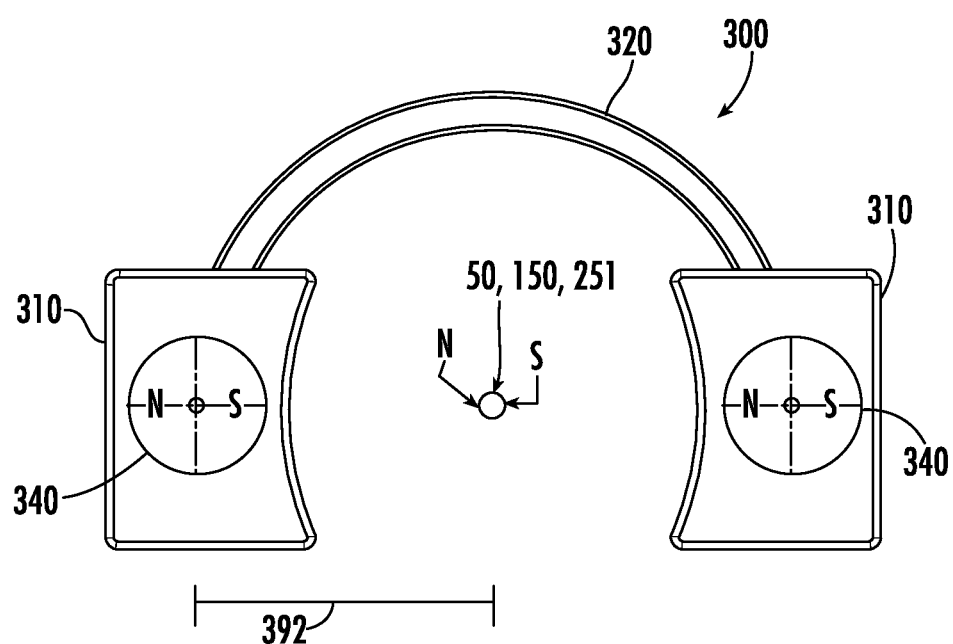
FIG. 25 illustrates an end view of the system shown in FIGS. 23 and 24 with only the inner magnet of the implantable reconfigurable bone adjustment device shown.

In one embodiment, depicted in FIGS. 23-25, the actuation unit 300 may include a pair of housings 310, an arcuate body 320 connecting the pair of housings 310, and a pair of outer magnets 340 mounted in the pair of housings 310, respectively. In FIGS. 23-25, the actuation unit 300 is illustrated in a position in which it partially surrounds the reconfigurable bone adjustment device 1, 101, 201, such that the outer magnets 340 are positioned on opposite sides of the internal magnet 50, 150, 251 of the reconfigurable bone adjustment device 1, 101, 201. The outer magnets 340 may, for example, be neodymium magnets, although other magnets may be employed as will be apparent to those skilled in the art. With the outer magnets 340 positioned on opposite sides of the internal magnet 50, 150, 251, and with each of the outer magnets 340 having an inward-facing side of one polarity aligned with a side of the inner magnet having the opposite polarity, the internal magnet 50, 150, 251 is magnetically coupled to the actuation unit 300. Thus, rotation of the actuation unit 300 about the longitudinal axis 90, 190, 290 of the reconfigurable bone adjustment device 1, 101, 201 results in a torque being applied to the internal magnet 50, 150, 251. As a result of the torque, the internal magnet 50, 150, 251 rotates about the longitudinal axis 90, 190, 290, thereby causing rotation of the threaded rod 70, 170, 245.

In certain forms, the arcuate body 320 may include an adjustment device which permits relative movement of the housings 310 in a direction transverse to the longitudinal axis 90, 190, 290 of the reconfigurable bone adjustment device 1, 101, 201. In such embodiments, the distance 392 (FIG. 25) between the center of the internal magnet 50, 150, 251 of the reconfigurable bone adjustment device 1, 101, 201 and the center of the outer magnets 340 of the actuation unit 300 may be adjustable in order to accommodate limbs of varying diameters. For example, the housings 310 may be moved further apart from one another to accommodate a limb having a larger diameter, and may be moved toward one another to increase the strength of the magnetic coupling when the limb has a smaller diameter.

In the illustrated embodiment, the outer magnets 340 are fixedly mounted in the housings 310, and rotation of the internal magnet 50, 150, 251 is achieved by rotating the actuating device 300 about the longitudinal axis 90, 190, 290 of the reconfigurable bone adjustment device 1, 101, 201. In other embodiments, the outer magnets 340 may be rotatably mounted in the housings 310 of the actuation unit 300. In such forms, rotation of the internal magnet 50, 150, 251 may be achieved by rotating the outer magnets while the actuation unit 300 remains stationary, as described, for example, in U.S. Pat. No. 8,777,947 to Zahrly et al, which is hereby incorporated herein by reference in its entirety. Alternatively, another embodiment of an external magnetic actuator is described in PCT Application No.: PCT/US17/68394, filed on Dec. 26, 2017, entitled Actuation System and Method for Orthopedic Implants with a Rotatable Internal Magnet, which is hereby incorporated herein by reference in its entirety.

After implantation of the reconfigurable bone adjustment device 1, 101, 201 in a patient, the external actuation unit 300 may be used at various times, per physician instructions, to non-invasively rotate the internal magnet 50, 150, 251 and the threaded rod 70, 170, 245 of the implanted reconfigurable bone adjustment device, as described herein. As will be appreciated, the ability of the actuation unit 300 to rotate the internal magnet 50, 150, 251 and the threaded rod 70, 170, 245 of the implanted reconfigurable bone adjustment device against the resistive forces of the bone callus and soft tissue is determined in part by the strength of the magnetic coupling between the internal magnet 50, 150, 251 of the reconfigurable bone adjustment device 1, 101, 201 and the outer magnets 340 of the external actuation unit 300. For patients with a large limb diameter, the distance 392 between the internal magnet 50, 150, 251 and the outer magnets 340 reduces the strength of the magnetic coupling, which limits the amount of torque that can be applied to the threaded rod 70, 170, 245 and the internal magnet 50, 150, 251 by the actuation unit 300. The ability of the actuation unit 300 to rotate the threaded rod 70, 170, 245 also depends in part upon the resistive frictional forces internal to the reconfigurable bone adjustment device 1, 101, 201, such as friction between the engaged threads of the threaded rod 170, 245 and the threaded block 119, 219 in the reconfigurable bone adjustment devices 1, 101, 201.

To address the risk of failure of the reconfigurable bone adjustment devices such as the devices described above, a variety of reconfiguration assembly embodiments are disclosed. The reconfiguration assembly embodiments are described in the context of a reconfigurable bone adjustment device that includes a first member configured for attachment to a first bone fragment, a second member configured for attachment to a second bone fragment, and a reconfiguration assembly configured to move the second member relative to the first member. The first member may be, for example and without limitation, the proximal body portion 110 of the IM limb lengthening nail 101 or the nail body 210 of the IM bone transport nail 201. The second member may be, for example and without limitation, the distal body portion 130 of the IM limb lengthening nail 101 or the carriage body 231 of the IM bone transport nail 201. The reconfiguration assembly may include a drive mechanism including a driver, wherein the drive mechanism is operable to controllably rotate the driver about a first axis of rotation, and a threaded rod having a proximal end coupled to the driver at a junction such that rotation of the driver causes rotation of the threaded rod about a second axis of rotation. As indicated above, the combination of the drive mechanism and the threaded rod is referred to herein as a "reconfiguration assembly," representative examples of which include, without limitation, the internal magnet 50 and the threaded rod 70 of the reconfigurable bone adjustment device 1; the internal magnet 150 and the threaded rod 170 of the IM limb lengthening nail 101; or the magnet housing assembly 240 and the threaded rod 245 of the IM bone transport nail 201. With reference to the IM bone transport nail 201, the second magnet housing cap 255 represents the driver of the reconfiguration assembly of the IM bone transport nail 201 to which the threaded rod 245 is affixed.

Figure 10:
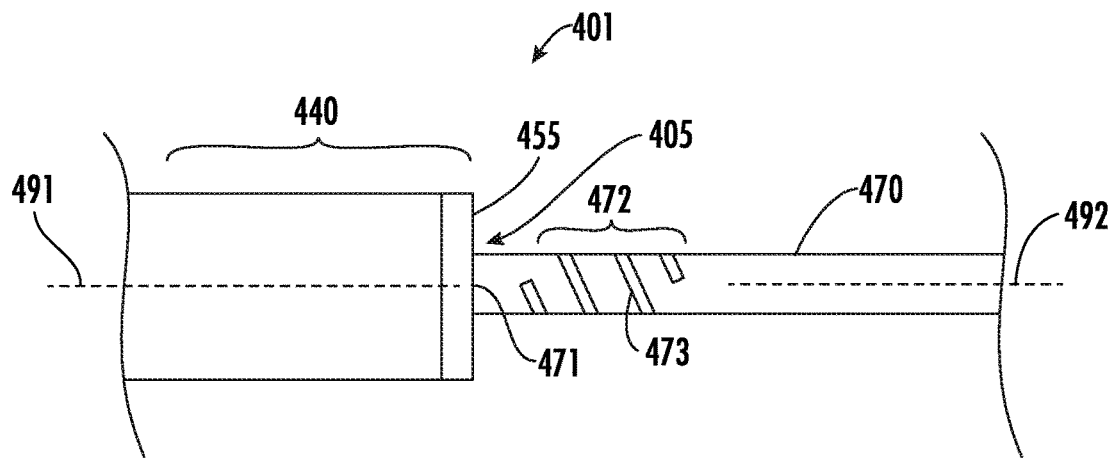
FIG. 10 illustrates a partial schematic representation of an example embodiment of a reconfiguration assembly used in connection with an implantable reconfigurable bone adjustment device.

In one embodiment, the reconfiguration assembly may be configured to withstand bending or eccentric loads that may be placed on the junction of the driver and the threaded rod of such a device. In another embodiment, the reconfiguration assembly may be configured to allow a degree of variation between the first axis of rotation and the second axis of rotation when the reconfiguration assembly is subjected to a bending or eccentric load. For example, FIG. 10 illustrates one variation of a reconfiguration assembly 401 that may be used in a reconfigurable bone adjustment device, in which a junction 405 at which a proximal end 471 of a threaded rod 470 is coupled to a driver 455 of a drive mechanism 440. The junction 405 can be any now known or hereafter developed junction including, for example, a welded joint. In some embodiments, the welded joint includes a threaded recess (not shown) in the driver 455 in which the proximal end 471 of the threaded rod 470 is advanced in threaded engagement, and then the threaded interface between the threaded recess and the portion of the threaded rod 470 at the interface are welded, such as by laser welding. In other embodiments, a segment of threaded rod 470 adjacent to the proximal end 471 is devoid of threads and is inserted into a smooth sided recess formed in the driver 455 and then welded in place. In yet other embodiments, the proximal end 471 of the threaded rod 470 may be welded in an abutting relationship with the driver 455, such as by friction welding. Other manners of affixing the proximal end 471 of the threaded rod 470 to the driver 455 are also contemplated. In the reconfiguration assembly 401, a proximal portion 472 of the threaded rod 470, which is located adjacent to the proximal end 471 of the threaded rod 470, includes a helical channel 473 formed therein. The incorporation of the helical channel 473 results in a decrease or elimination of bending stresses on or at the junction 405, which may occur, for example, when the rotational axis 491 of drive mechanism 440 (e.g., a first axis of rotation) is not in exact alignment with rotational axis 492 of threaded rod 470 (e.g., a second axis of rotation).

Figure 11:
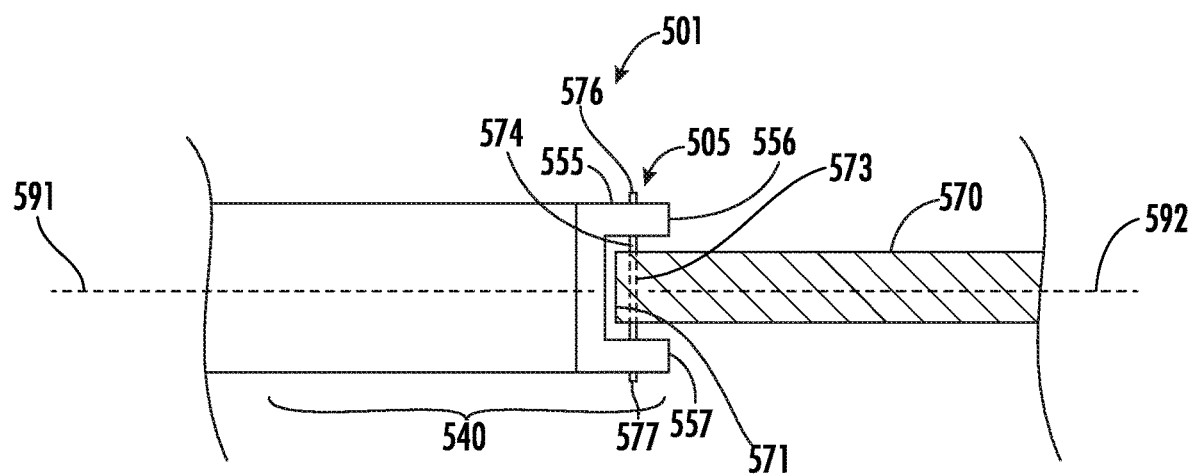
FIG. 11 illustrates a partial schematic representation of an alternate example embodiment of a reconfiguration assembly used in connection with an implantable reconfigurable bone adjustment device.

Referring to FIG. 11, an alternate embodiment of a reconfiguration assembly for allowing a degree of variation between a first axis of rotation and a second axis of rotation is provided. In the reconfiguration assembly 501, illustrated in FIG. 11, the proximal end 571 of the threaded rod 570 may be coupled to the driver 555 of the drive mechanism 540 via a dynamic joint 505. In the embodiment shown, the dynamic joint 505 may be a pinned joint including the driver 555. As shown, the driver 555 may include first and second projections 556, 557 spaced sufficiently apart to provide clearance for the proximal end 571 of the threaded rod 570. The threaded rod 571 includes a radial aperture 573 near the proximal end 571 thereof to receive a pin 574. The pin 574 may include first and second ends 576, 577. In use, the pin 574 may be inserted into the radial aperture 573 formed in the threaded rod 570 such that the first and second ends 576, 577 of the pin 574 extend from the radial aperture 573 and into engagement with the first and second projections 556, 557, respectively. In this manner, during use, the threaded rod 570 does not transfer moments to the driver 555. This arrangement therefore also results in a decrease or elimination of bending stresses on the drive mechanism 540, which may otherwise occur, for example, when the rotational axis 591 of the drive mechanism 540 (e.g., a first axis of rotation) is not in exact alignment with the rotational axis 592 of the threaded rod 570 (e.g., a second axis of rotation). In alternate embodiments (not shown), the dynamic joint 505 can take the form of a ball joint or a universal joint rather than a pinned joint.

In another manner of addressing the risk of failure of reconfigurable bone adjustment devices such as the reconfigurable bone adjustment devices 1, 101, 201 described above, bending moments and stresses on a junction between the driver and the threaded rod may be lessened or eliminated by positioning a collar between the driver and the second body portion or member of the reconfigurable bone adjustment device such that rotation of the threaded rod in a first direction exerts a compressive force between a distal surface of the collar and a proximal end of the second body portion or member to move the second body portion or member relative to the first body portion or member.

Figure 12:
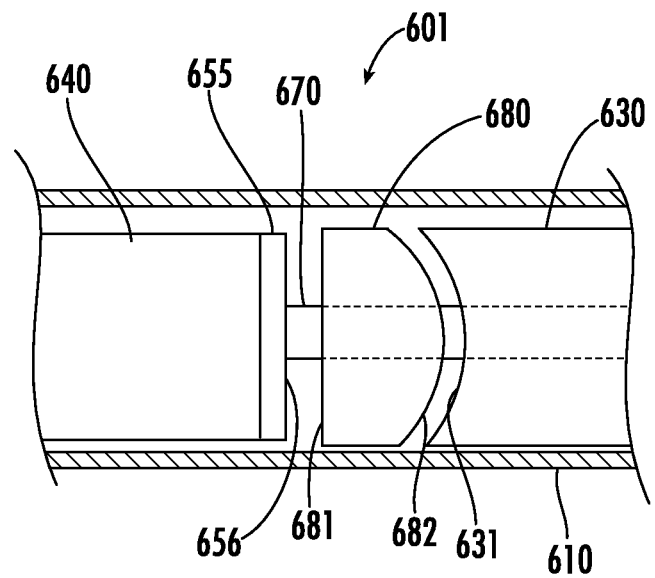
FIG. 12 illustrates a partial schematic representation of an alternate example embodiment of a reconfiguration assembly used in connection with an implantable reconfigurable bone adjustment device.

For example, FIG. 12 illustrates one variation of a reconfiguration assembly 601 for use in a reconfigurable bone adjustment device in which a collar 680 is positioned between a driver 655 and a second body portion 630 of the reconfigurable bone adjustment device. For context, FIG. 12 also depicts the first body portion 610 of the reconfigurable bone adjustment device. While the driver 655, the collar 680 and the second body portion 630 are shown in FIG. 12 with spaces therebetween, it is to be understood that in normal operation, rotation of the threaded rod 670 in a first direction will cause the driver 655 to exert a compressive force on the collar 680, which in turn exerts a compressive force on the second body portion 630. Thus, in normal use, a distal surface 656 of the driver 655 will be in contact with a proximal surface 681 of collar 680 and a distal surface 682 of the collar 680 will be in contact with a proximal surface 631 of the second body portion 630. In one embodiment, each of surfaces 656, 681, 682, 631 may be generally flat. In another embodiment, a bearing or bushing (not shown) may be positioned between the distal surface 656 of the driver 655 and the proximal surface 681 of collar 680. In another embodiment, a bearing or bushing may be positioned between the distal surface 682 of the collar 680 and the proximal surface 631 of the second body portion 630. In still another embodiment, two bearings or bushings may be present (or one of each), one positioned between the distal surface 656 of the driver 655 and the proximal surface 681 of collar 680 and another positioned between the distal surface 682 of the collar 680 and the proximal surface 631 of the second body portion 630. In yet another embodiment, one or more of the surfaces 656, 681, 682, 631 may include a contour that is not flat. In embodiments in which one or more of the surfaces 656, 681, 682, 631 has a contour that is not flat, it is preferred for the contacting surfaces, that is, the distal surface 656 of the driver 655 and the proximal surface 681 of collar 680, or the distal surface 682 of the collar 680 and the proximal surface 631 of the second body portion 630 (which can be referred to as "surface pairs") to have complementary shapes, it being understood that at least one of the surface pairs must be configured to allow relative rotation between the driver 655 and the collar 680, or between the collar 680 and the second body portion 630, or both.

In the embodiment shown, the collar 680 may include a convex distal surface 682 (also referred to as a "domed surface") and the second body portion 630 may include a complementary concave proximal surface 631. The interface of the convex distal surface 682 and the concave proximal surface 631 is capable of transmitting a compressive force substantially in the direction of a longitudinal axis of the threaded rod 670 from the collar 680 to the second body portion 630 during normal use of the reconfigurable bone adjustment device that includes the reconfiguration assembly 601. It is, of course, understood that the convex distal surface 682 and the concave proximal surface 631 can be symmetrical, but in some embodiments, are not symmetrical.

Figure 13:
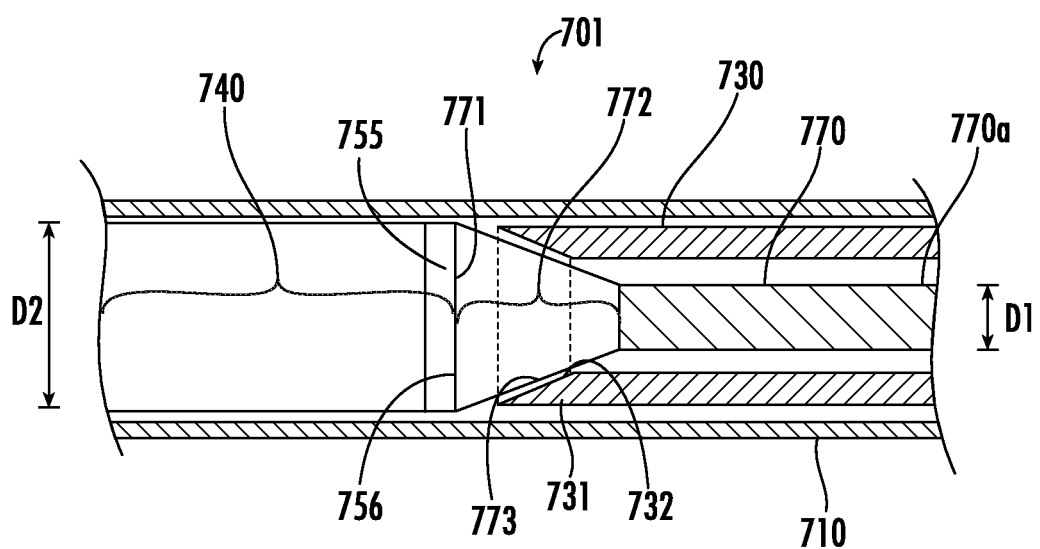
FIG. 13 illustrates a partial schematic representation, in partial cross section, of an alternate example embodiment of a reconfiguration assembly used in connection with an implantable reconfigurable bone adjustment device.

In another manner of addressing the risk of failure of reconfigurable bone adjustment devices such as the reconfigurable bone adjustment devices 1, 101, 201 described above, bending moments and stresses on a junction between the driver and the threaded rod may be lessened or eliminated by utilizing a threaded rod that has a first diameter along a major portion of its length and a second or proximal segment having a second diameter that is greater than the first diameter. The larger diameter, second or proximal segment of the threaded rod may be integrally formed with the smaller diameter portion of the threaded rod. In one embodiment, the larger diameter, second or proximal segment may include a tapered segment located between the major portion of the first diameter and the proximal end of the threaded rod. That is, with reference to FIG. 13, the threaded rod 770 of the reconfiguration assembly 701 may include a first segment 770a having a first diameter D1 along a threaded portion. The threaded rod 770 may also include a second segment 772, located at a proximal end of the threaded rod adjacent to the driver 755. The second or proximal segment 772 may include a second diameter D2, where the second diameter D2 is greater than the first diameter D1. In one embodiment, the first segment 770a includes threads and constitutes a majority of the overall length of the threaded rod 770. In the embodiment shown, the second or proximal segment 772 may include a tapered section that tapers from the first diameter D1, where the second or proximal segment 772 meets the first segment 770a of the threaded rod 770, to a second diameter D2 at a proximal end 771 of the second or proximal segment 772. For context, FIG. 13 also depicts the first body portion 710 and the second body portion 730. In use, rotation of the threaded rod 770 in a first direction causes the second or proximal tapered segment 772 to exert a compressive force on the proximal end 731 of the second body portion 730. Because normal operation of the reconfigurable bone adjustment device requires relative rotation between the second or proximal tapered segment 772 and the second body portion 730, a bearing or bushing (not shown) may be positioned between an outer surface 773 of the second or proximal tapered segment 772 and an outer surface 732 at the proximal end 731 of the second body portion 730.

Because rotation of the threaded rod 770 in the first direction exerts a tensile load on a load bearing portion of the threaded rod 770 only at the location where the second body portion 730 contacts the second or proximal tapered segment 772 to the axial location where the threaded rod 770 engages a threaded mating component of the first body portion 710 (such as, for example, the threaded block 119 of the IM limb lengthening nail 101), loading of the reconfigurable bone adjustment device that includes the reconfiguration assembly 701 does not place an axial load on the junction of the proximal end 771 of the second or proximal tapered segment 772 and the distal surface 756 of the driver 755.

The proximal end 771 of the second or proximal tapered segment 772 can be coupled to the driver 755 in any desirable manner. In one embodiment, the proximal end 771 of the second or proximal tapered segment 772 may be coupled to the driver 755 by friction welding. In the embodiment shown, both of these surfaces are generally circular and have generally the same diameter; however, the surfaces can have different sizes and different shapes, if desired. Friction welding of the surfaces will provide a strong joint able to withstand the torque transmitted from the drive mechanism 740 to the threaded rod 770 through the joint.

Figure 14:
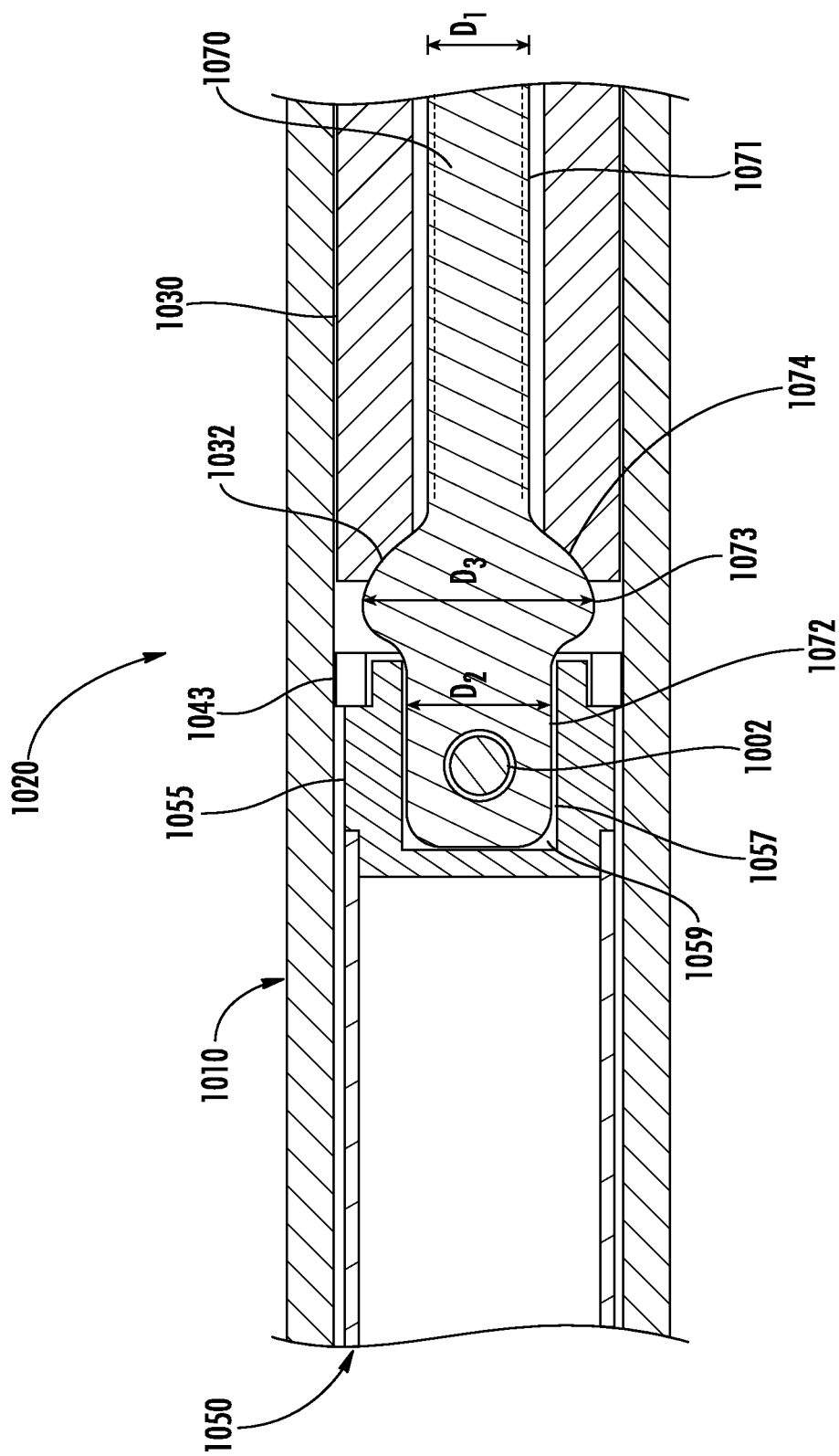
FIG. 14 illustrates a partial schematic representation, in partial cross section, of an alternate example embodiment of a reconfiguration assembly used in connection with an implantable reconfigurable bone adjustment device.

FIG. 14 illustrates another embodiment of a reconfiguration assembly that utilizes a threaded rod having different diameters to lessened or eliminate bending moments and stresses on a junction between the driver and the threaded rod. As illustrated, and as previously described, the implantable reconfigurable bone adjustment device may include a first body 1010 and a second body 1030 at least partially received within first body 1010. For example, as illustrated, the implantable reconfigurable bone adjustment device may be an IM limb lengthening nail having a proximal outer body portion 1010, a distal inner body portion 1030, and a threaded rod 1070 operatively associated with the proximal outer body portion 1010 and the distal inner body portion 1030. In use, rotation of the threaded rod 1070 causes the proximal outer body portion 1010 and the distal inner body portion 1030 to move with respect to one another. However, it is envisioned that the implantable reconfigurable bone adjustment device may be provided in other forms including, for example, IM bone transport nail.

As previously mentioned, the proximal outer body portion 1010 may house a drive mechanism (e.g., an internal magnet) 1050 operatively coupled to the threaded rod 1070 via a reconfiguration assembly 1020. In use, the drive mechanism (e.g., internal magnet) 1050 may include or be operatively associated with a driver 1055, which may be in the form of a magnetic housing cap. The driver 1055 may be coupled to the threaded rod 1070 by any suitable means. As illustrated, the driver 1055 may be coupled to the threaded rod 1070 (e.g., to a second or proximal segment 1072 of the threaded rod 1070) via a pin connection 1002.

As previously mentioned, rotation of the drive mechanism (e.g., an internal magnet) 1050 via, for example, an external rotating magnetic field, which may be applied, for example, using an external magnetic actuator (as described further below), results in rotation of the threaded rod 1070, which causes the distal inner body 1030 to move with respect to the proximal outer body 1010.

The threaded rod 1070 includes a first segment 1071 extending along a major portion of its length. The first segment 1071 may have a first diameter $D_1$. In addition, the first segment 1071 may include external threads along all or a majority of its length for directly or indirectly engaging an inner surface of the distal inner body 1030. In addition, the threaded rod 1070 may include a second or proximal segment 1072 having a second diameter $D_2$ that is greater than the first diameter $D_1$. The larger diameter, second or proximal segment 1072 of the threaded rod 1070 may be integrally formed with the smaller diameter first segment 1071 of the threaded rod 1070. In one embodiment, the threaded rod 1070 may also include a third segment 1073 having an enlarged spherical or bulbed segment having a third diameter $D_3$. The third diameter $D_3$ being larger than the first diameter $D_1$ and the second diameter $D_2$. As illustrated, the third segment 1073 may be located in-between the first and second segments 1071, 1072. The second and third segments 1072, 1073 may be devoid of any external threading. That is, the threads preferably cease prior to the corresponding contacting surfaces between the enlarged spherical or bulbed segment 1073 and the proximal end 1032 of the distal inner body 1030 (as will be described in greater detail below).

By providing an enlarged spherical or bulbed segment 1073 having a third diameter $D_3$ where the third diameter $D_3$ is larger than the first diameter $D_1$ and the second diameter $D_2$ enables the second segment $D_2$ to be made smaller than otherwise possible if the enlarged spherical or bulbed segment 1073 was omitted. That is, for example, by providing the enlarged spherical or bulbed segment 1073, allows for a smaller second segment 1072, which enables the driver 1055 to have thicker walls.

In use, rotation of the drive mechanism (e.g., internal magnet) 1050 rotates the driver 1055, which in turn, rotates the threaded rod 1070. Rotation of the threaded rod 1070 in a first direction causes an outer contacting surface 1074 of the enlarged spherical or bulbed segment 1073 to contact and exert a compressive force on a proximal end 1032 of the distal inner body 1030.

The contacting surfaces between the enlarged spherical or bulbed segment 1073 and the proximal end 1032 of the distal inner body 1030 preferably include corresponding concave and convex articulating surfaces. In one embodiment, the articulating, contact surfaces between the enlarged spherical or bulbed segment 1073 and the proximal end 1032 of the distal inner body 1030 are essentially spherical.

As a result, the axial load passes through the articulating surface. Moreover, as a result of the corresponding concave and convex articulating surfaces, a ball-joint type connection may be formed. In use, the articulating, contacting surfaces enable some rotation between the enlarged spherical or bulbed segment 1073 and the proximal end 1032 of the distal inner body 1030. This connection leads to improved articulation, weight bearing, and improved distraction.

In one embodiment, clearances may be provided between the threaded rod 1070 and the driver 1055 (e.g., the distal magnet housing cap). As such, the threaded rod 1070 is no longer rigidly fixed to the driver 1055 (e.g., the distal magnet housing cap). That is, as illustrated, by incorporating a pin connection, gaps or spaces 1057, 159 may be incorporated between the second or proximal segment 1072 of the threaded rod 1070 and the driver 1055, allowing for some movement of the threaded rod 1070 about the pin axis and around the pin 1002. By enabling some movement of the threaded rod 1070 allows for easier bending of the nail.

As illustrated, the reconfigurable bone adjustment device 1020 may also include a bushing 1043, as previously mentioned. The busing 1043 may be positioned at a distal end of the driver 1055. The bushing 1043 positioned between the driver 1055 and the inner surface of the proximal outer body 1010, thus facilitating rotation of the driver 1055 within the proximal outer body 1010.

In one embodiment, the threads formed on the threaded rod 1070 may include a surface treatment. In addition, the corresponding articulating, contact surfaces between the enlarged spherical or bulbed segment 1073 and the proximal end 1032 of the distal inner body 1030 may include a surface treatment. The surface treatment could be any suitable treatment that increases lubricity, for example, an amorphous diamond-like carbon (DLC), plasma immersion ion implantation, PA-CVD, PVD, etc.

Figure 15:
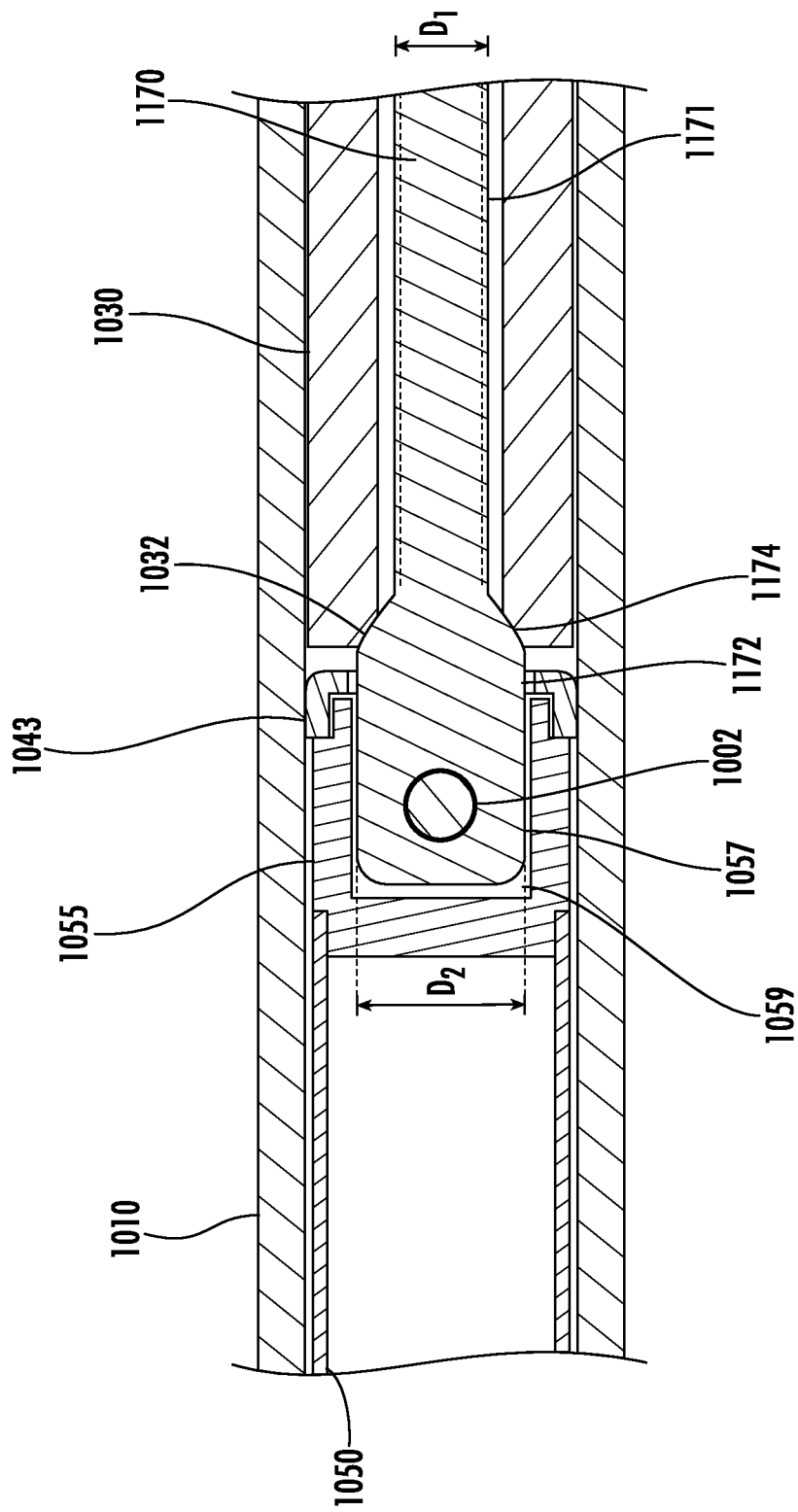
FIG. 15 illustrates a partial schematic representation, in partial cross section, of an alternate example embodiment of a reconfiguration assembly used in connection with an implantable reconfigurable bone adjustment device.
Figure 16:
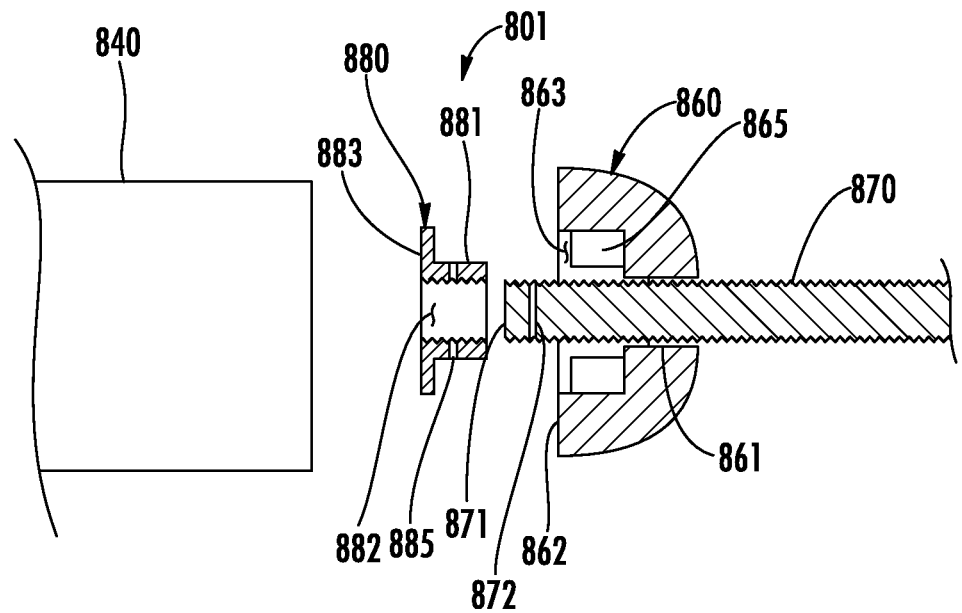
FIG. 16 illustrates an exploded partial schematic representation, in partial cross section, of an alternate example embodiment of a reconfiguration assembly used in connection with an implantable reconfigurable bone adjustment device.
Figure 17:
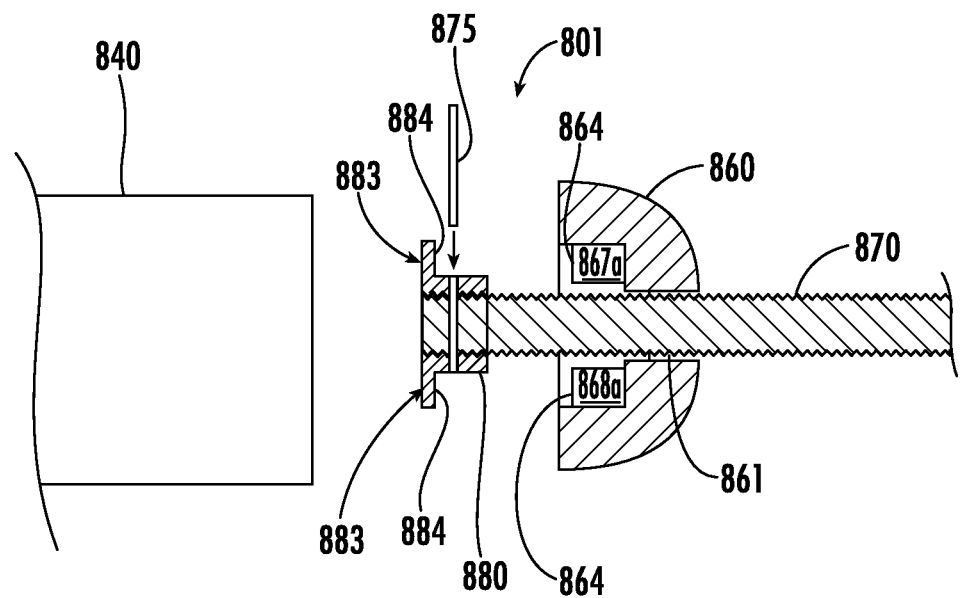
FIG. 17 illustrates an alternate exploded partial schematic representation, in partial cross section, of the reconfiguration assembly shown in FIG. 16.
Figure 18:
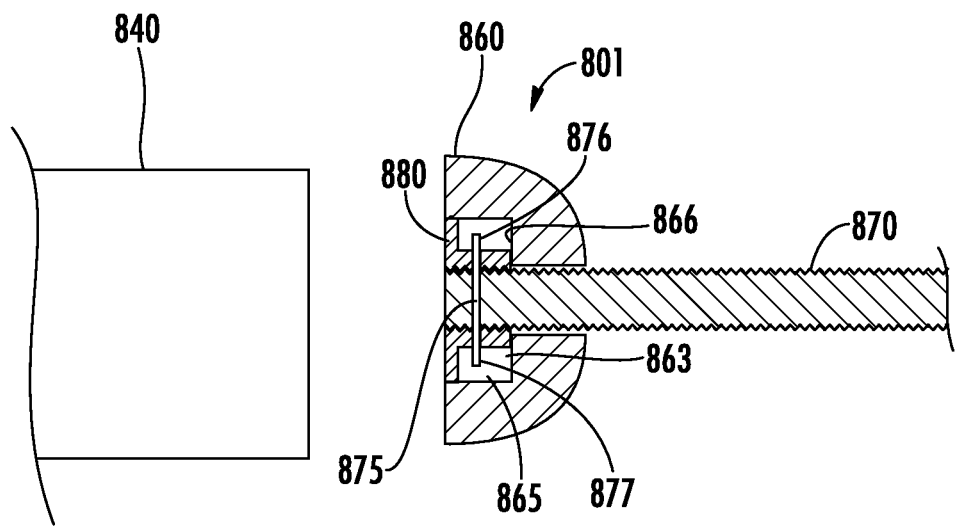
FIG. 18 illustrates an alternate partial schematic representation, in partial cross section, of the reconfiguration assembly shown in FIG. 16.
Figure 19:
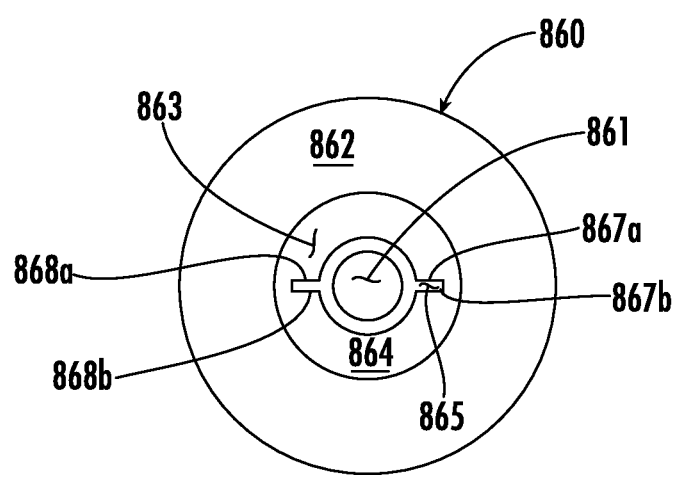
FIG. 19 illustrates a proximal view of an example embodiment of a spacer component used in connection with the reconfiguration assembly shown in FIGS. 16-18.

FIG. 15 illustrates another embodiment of a reconfiguration assembly that utilizes a threaded rod having different diameters to lessened or eliminate bending moments and stresses on a junction between the driver and the threaded rod. The embodiment illustrated in FIG. 15 is substantially similar to the embodiment described and illustrated above in connection with FIG. 14, except as described herein.

Referring to FIG. 15, the threaded rod 1170 includes a first segment 1171 extending along a major portion of its length. The first segment 1171 may have a first diameter $D_1$. In addition, the first segment 1171 may include external threads along all or a majority of its length for directly or indirectly engaging an inner surface of the distal inner body 1030. In addition, the threaded rod 1170 may include a second or proximal segment 1172 having a second diameter $D_2$ that is greater than the first diameter $D_1$. The larger diameter, second or proximal segment 1172 of the threaded rod 1170 may be integrally formed with the smaller diameter first segment 1171 of the threaded rod 1170. The second segment 1172 may be devoid of any external threading. That is, the threads preferably cease prior to the corresponding contacting surfaces between the enlarged second segment 1172 and the proximal end 1032 of the distal inner body 1030.

In use, rotation of the drive mechanism (e.g., internal magnet) 1050 rotates the driver 1055, which in turn, rotates the threaded rod 1170. Rotation of the threaded rod 1170 in a first direction causes an outer contacting surface 1174 of the enlarged second segment 1172 to contact and exert a compressive force on a proximal end 1032 of the distal inner body 1030.

The contacting surfaces between the enlarged second segment 1172 and the proximal end 1032 of the distal inner body 1030 preferably include corresponding concave and convex articulating surfaces. In one embodiment, the articulating, contact surfaces between the enlarged second segment 1172 and the proximal end 1032 of the distal inner body 1030 are essentially spherical.

As a result, the axial load passes through the articulating surface. Moreover, as a result of the corresponding concave and convex articulating surfaces, a ball joint type connection may be formed. In use, the articulating, contacting surfaces enable some rotation between the enlarged second segment 1172 and the proximal end 1032 of the distal inner body 1030. This connection leads to improved articulation, weight bearing, and improved distraction.

In one embodiment, clearances may be provided between the threaded rod 1170 and the driver 1055 (e.g., the distal magnet housing cap). As such, the threaded rod 1070 is no longer rigidly fixed to the driver 1055 (e.g., the distal magnet housing cap). That is, as illustrated, by incorporating a pin connection, gaps or spaces 1057, 159 may be incorporated between the second or proximal segment 1172 of the threaded rod 1170 and the driver 1055, allowing for some movement of the threaded rod 1170 about the pin axis and around the pin 1002. By enabling some movement of the threaded rod 1170 allows for easier bending of the nail.

As will be described by one of ordinary skill in the art, threaded rod 1170 allows for easier manufacturability as compared to threaded rod 1070. However, as a consequence, the driver 1055 may have thinner walls when used in combination with threaded rod 1170 as compared to threaded rod 1060.

In still another manner of addressing the risk of failure of reconfigurable bone adjustment devices such as the reconfigurable bone adjustment devices 1, 101, 201 described above, there is provided a reconfigurable bone adjustment device in which the junction of the driver and the threaded rod includes a spacer component that is configured to receive the proximal end of the threaded rod, capture the proximal end of the threaded rod, drive rotation of the threaded rod and localize the tensile axial load on the threaded rod. In one embodiment, the junction may also include a stop component that is coupled to the threaded rod adjacent to the proximal end of the threaded rod and is dimensioned to be captured in a cavity in the spacer component. The stop component may be co-rotationally coupled to the threaded rod and the spacer component may be co-rotationally affixed to the drive mechanism. The stop component and the spacer component are configured such that torque applied by the drive mechanism transfers through one or more interfacing surfaces between the spacer component and the stop component to transfer torque to the threaded rod, thereby rotating the threaded rod. In use, rotation of the threaded rod in a first direction exerts a compressive force at an interface between a distal surface of the spacer component and the proximal end of the second body portion to move the second body portion relative to the first body portion.

FIGS. 16-19 illustrate one embodiment of a reconfiguration assembly that includes a spacer component and a stop component. In the reconfiguration assembly 801, a spacer component 860 includes a bore 861 that is dimensioned for passage of a threaded rod 870 therethrough. The spacer component 860 may also include a cavity 863 that opens, for example, towards a proximal end or side 862 of the spacer component 860. The cavity 863 may be dimensioned to capture a stop component 880, which is coupled to the threaded rod 870 adjacent to a proximal end 871 thereof. In the embodiment shown, the stop component 880 may include a body 881 defining an axial bore 882 having internal threads complementary to the external threading of the threaded rod 870 and dimensioned to threadingly engage the threaded rod 870 at a position adjacent the proximal end 871 of the threaded rod 870. It is to be understood, however, that the internal threading of the axial bore 882 is optional, and other means can be used to affix the stop component 880 to the threaded rod 870 at a position adjacent the proximal end 871 of the threaded rod 870 as long as the other means for affixing the stop component 880 to the threaded rod 870 is operable to bear an axial load between the stop component 880 and the threaded rod 870 under loads encountered during use of an implantable reconfigurable bone adjustment device that includes the reconfiguration assembly 801. In one embodiment, the stop component 880 may be coupled to the threaded rod 870 by welding.

The stop component 880 may also include a flange 883, for example, at a proximal end thereof, that extends laterally beyond the body 881, i.e., has a radial dimension greater than a radial dimension of the body 881. In use, the cavity 863 formed in the spacer component 860 may be dimensioned to receive the stop component 880 and the spacer component 860 may include a shoulder surface 864 dimensioned to contact a distal surface 884 of the proximal flange 883 when the stop component 880 is received in the cavity 863.

The body 881 of the stop component 880 may include a first radial aperture 885 and the threaded rod 870 may include a second radial aperture 872 near the proximal end 871 of the threaded rod 870. The first and second radial apertures 885, 872 are positioned such that they can be aligned to receive a pin 875 to couple the stop component 880 to the threaded rod 870 and limit relative rotational movement between the threaded rod 870 and the stop component 880. In this embodiment, the spacer component 860 may also include a radial channel 865 (FIG. 19) configured to receive and retain the respective ends of the pin 875. That is, in use, the pin 875 may have a length greater than the outer dimension of the body 881 of the stop component 880 and in the assembled device, the pin 875 may be positioned such that each end 876, 877 of the pin 875 extends beyond the body 881 of the stop component 880 on each side of the body 881. As is seen most clearly in FIG. 18, the radial channel 865 of the spacer component 860 has sufficient depth, relative to the position of the radial apertures 885, 872, such that the pin 875 does not contact a distal surface 866 of the radial channel 865 when the stop component 880 is received in the cavity 863 of the spacer component 860. Therefore, the pin 875 does not bear an axial load when an implantable reconfigurable bone adjustment device that includes the reconfiguration assembly 801 is in use and under loads encountered during normal use. The pin 875 does, however, contact one or more side surfaces 867a, 867b, 868a, 868b of the radial channel 865 when the reconfiguration assembly 801 is rotated by the drive mechanism 840, thereby transferring torque from the spacer component 860 to the threaded rod 870.

Figure 20:
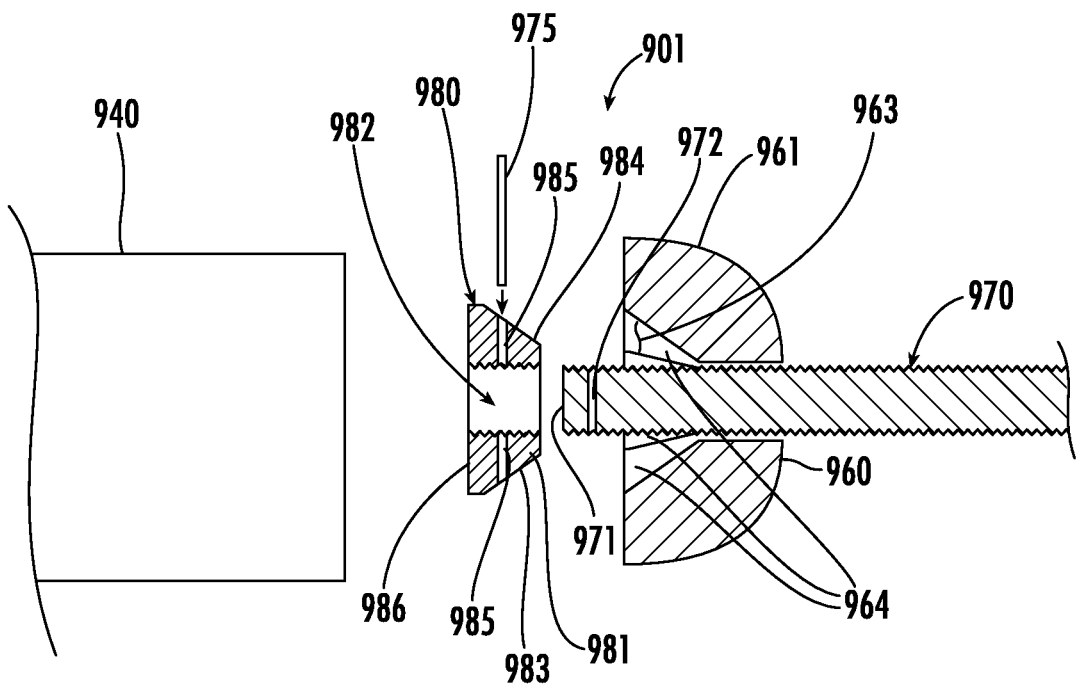
FIG. 20 illustrates an exploded partial schematic representation, in partial cross section, of an alternate example embodiment of a reconfiguration assembly used in connection with an implantable reconfigurable bone adjustment device.
Figure 21:
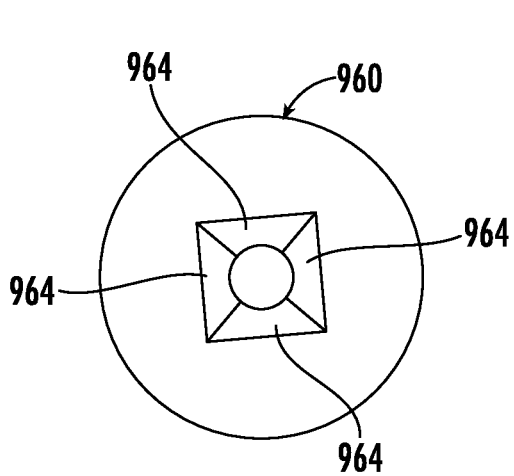
FIG. 21 illustrates a proximal view of an example embodiment of a spacer component used in connection with the reconfiguration assembly shown in FIG. 20.

In an alternative embodiment, depicted in FIGS. 20 and 21, a spacer component 961 and a stop component 980 of a reconfiguration assembly 901 may be configured such that a distal side 983 of the stop component 980 has a geometric shape and defines a plurality of distal surfaces 984. The stop component 980 may include an axial bore 982 having internal threads complementary to the threading of the threaded rod 970 and dimensioned to threadingly engage the threaded rod 970 at a position adjacent a proximal end 971 of the threaded rod 970. It is to be understood, however, that internal threading of the axial bore 982 is optional, and other means can be used to affix the stop component 980 to the threaded rod 970 at a position adjacent the proximal end 971 of the threaded rod 970 as long as the other means for affixing the stop component 980 to the threaded rod 970 is operable to bear an axial load between the stop component 980 and the threaded rod 970 under loads encountered during use of an implantable reconfigurable bone adjustment device that includes the reconfiguration assembly 901. In one embodiment, the stop component 980 may be coupled to the threaded rod 970 by welding.

In the illustrated embodiment, the stop component 980 may include a first radial aperture 985 and the threaded rod 970 may include a second radial aperture 972 near the proximal end 971 of the threaded rod 970. As with the embodiments described above, the first and second radial apertures 985, 972 are positioned such that they can be aligned to receive a pin 975 to couple the stop component 980 to the threaded rod 970 and limit relative rotational movement between the threaded rod 970 and the stop component 980. In the reconfiguration assembly 901, however, the pin 975 need not extend past the outer dimension of the stop component 980 because torque is transmitted from the spacer component 960 to the stop component 980 by way of the complementary surfaces thereof, which form interfaces capable of transmitting torque. As an alternative to placing the pin 975, or in addition to placing the pin 975, as described above, the body 981 of the stop component 980 optionally can be welded to the threaded rod 970 after the stop component 980 is advanced onto the threaded rod 970 to a desired position adjacent the proximal end 971 of the threaded rod 970.

The spacer component 960 may include a cavity 963 with a plurality of contact surfaces 964 dimensioned to complement the plurality of distal surfaces 984 of the stop component 980 such that, when the stop component 980 is received within the cavity 963, the contact surfaces 964 of the cavity 963 contact the distal surfaces 984 of the stop component 980 and permit torque that is applied to the spacer component 960 to be transferred to the stop component 980 to thereby rotate the threaded rod 970. In one embodiment, the spacer component 960 may have a pyramidal shape in which the proximal side 986 of the stop component 980 represents the base of the pyramid. It is, of course, understood that the pyramidal shape will be a partial pyramidal shape because the sides of the pyramidal shape will not come to a point due to the presence of the axial bore 982 through the stop component 980. In the embodiment depicted in FIGS. 20 and 21, the proximal side 986 of the stop component 980 has a square shape, giving the stop component 980 a four-sided pyramidal shape, and the cavity 963 formed in the spacer component 960 has four contact surfaces 964 that complement the converging distal sides 984 of the pyramidal stop component 980.

Figure 22:
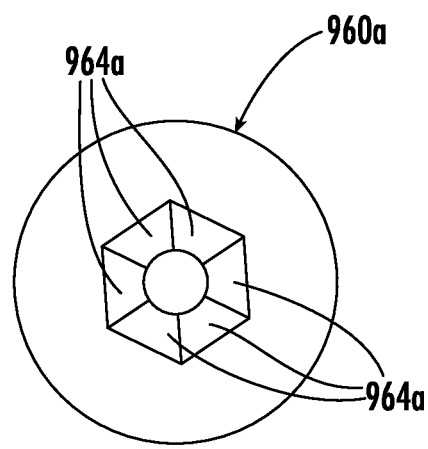
FIG. 22 illustrates a proximal view of an alternate example embodiment of a spacer component used in connection with the reconfiguration assembly shown in FIG. 20.

FIG. 22 depicts a spacer component 960a of another embodiment configured to receive a stop component for whose proximal side has a generally hexagonal shape and which stop component has a six-sided pyramidal shape. Thus, the spacer component 960a defines a cavity with six contact surfaces 964a that complement the six converging distal sides of the pyramidal stop component. As will be appreciated by a person of ordinary skill in the art, the square and hexagonal embodiments are provided only as examples, it being understood that a wide variety of geometric shapes, such as, for example, three-sided pyramids or five-sided pyramids, pyramids having bases with trapezoidal shapes and also non-geometric shapes, can be used to form alternative stop component embodiments having interfacing surfaces that complement contact surfaces of spacer component embodiments that are operable to exert torsional forces from spacer component to stop component and threaded rod.

Orthopedic implants and prosthetics such as reconfigurable bone adjustment devices described herein typically are formed of a biocompatible metal. Medical grade cobalt-chromium (CoCr) alloys such as cobalt-chromium-molybdenum (CoCrMo) and cobalt-chromium-iron (CoCrFe) are among the most suitable metallic biomaterials, particularly for weight-bearing implants. These alloys typically exhibit high mechanical properties, adequate corrosion resistance, and acceptable biocompatibility. In one embodiment, a reconfigurable bone adjustment device according to the present disclosure is formed of a cobalt-chromium-iron (CoCrFe) alloy. In another embodiment, the alloy comprises a 40Co-20Cr-16Fe-15Ni-7Mo alloy. It should be appreciated however that the reconfigurable bone adjustment devices may be manufactured from any suitable material.

As will be appreciated from the descriptions herein and the associated Figures, a wide variety of embodiments are contemplated by the present disclosure, examples of which include, without limitation, the following:

The present disclosure provides a reconfigurable bone adjustment device, and associated kits, systems and methods. In one embodiment, the reconfigurable bone adjustment device may include a first body portion or member configured for attachment to a first bone fragment, a second body portion or member configured for attachment to a second bone fragment, and a reconfiguration assembly configured to move the second body portion or member relative to the first body portion or member. The reconfiguration assembly may include a drive mechanism including a driver and a threaded rod having a proximal end coupled to the driver at a junction. In use, the drive mechanism is operable to controllably rotate the driver. In addition, rotation of the driver causes rotation of the threaded rod.

In one embodiment, the reconfigurable bone adjustment device may be an intramedullary limb lengthening nail. In another embodiment, the reconfigurable bone adjustment device may be a bone transport nail. The reconfiguration assembly operates by reducing applied stresses, such as axial forces, torsional forces, bending moments and/or eccentric moments on the driver/threaded rod junction and/or by configuring the junction in a manner whereby one or more of the axial forces, torsional forces, bending moments and/or eccentric moments is isolated away from the junction.

In one embodiment, the driver has a first axis of rotation, the threaded rod has a second axis of rotation and the reconfiguration assembly is configured to allow a degree of variation between the first axis of rotation and the second axis of rotation when the reconfiguration assembly is subjected to a bending load (e.g., when a proximal portion of the threaded rod is under an axial load and the reconfiguration assembly is subjected to a bending or eccentric load). In one embodiment, this may be accomplished by providing a helical channel in a segment of the threaded rod adjacent to a proximal end of the threaded rod. That is, for example, the junction may include a welded joint between the proximal end of the threaded rod and the driver, and a proximal portion of the threaded rod adjacent the proximal end of the threaded rod may include a helical channel formed therein. In another embodiment, this may be accomplished by providing a dynamic joint connecting the threaded rod to the driver. Examples of dynamic joints include, but are not limited to, pinned joints, ball joints and universal joints.

In another embodiment, the reconfigurable bone adjustment device may be constructed such that the threaded rod engages a threaded mating component of the first member such that rotation of the threaded rod in a first direction causes the driver to exert a compressive force on a proximal end of the second member. Moreover, rotation of the threaded rod in the first direction exerts a tensile load on a load bearing portion of the threaded rod extending from the junction to the threaded mating component. A collar may be positioned between the driver and the second member such that rotation of the threaded rod in the first direction exerts a compressive force between a distal surface of the collar and a proximal end of the second member to move the second member relative to the first member.

In one embodiment, the collar may be in the form of a domed collar. That is, the collar may include a convex distal surface and the proximal end of the second member may include a complementary concave surface, the convex distal surface of the collar and the complementary concave surface of the second member forming an interface for transmitting a compressive force substantially in the direction of a longitudinal axis of the threaded rod from the collar to the second member.

In another embodiment, the threaded rod may have a first diameter along a major portion of its length. The threaded rod may also include a proximal segment having a second diameter greater than the first diameter. The proximal segment may be integrally formed with the threaded rod. The proximal segment may be axially located between the portion of the threaded rod that has the first diameter and the proximal end of the threaded rod. The reconfigurable bone adjustment device may be constructed such that the threaded rod engages a threaded mating component of the first member, rotation of the threaded rod in a first direction causes the proximal segment to exert a compressive force on a proximal end of the second member, and rotation of the threaded rod in the first direction exerts a tensile load on a load bearing portion of the threaded rod that extends from the proximal segment to the threaded mating component such that the axial load is not placed on the junction. In one embodiment, the proximal segment is a proximal tapered segment, wherein the threaded rod tapers from the first diameter at the major portion of the threaded rod to a second diameter at the proximal end of the threaded rod, the second diameter being greater than the first diameter. In another embodiment, the proximal segment forms a shoulder surface against which the proximal end of the second member rests.

In another embodiment, the junction may include a stop component coupled to the threaded rod adjacent to the proximal end of the threaded rod and a spacer component defining a bore dimensioned to permit passage of the threaded rod therethrough. The spacer component may include a distal surface configured to abut or contact a proximal end of the second member and a proximal side including a cavity dimensioned to receive and capture the stop component. The reconfigurable bone adjustment device may be constructed such that the threaded rod engages a threaded mating component of the first member, rotation of the driver in the first direction causes co-rotation of the spacer component and the threaded rod in the first direction to exert a compressive force at an interface between a distal surface of the spacer component and the proximal end of the second member to move the second member relative to the first member. In this embodiment, the axial load is isolated away from the interface between the driver and the spacer component. The stop component can have a wide variety of shapes. In one embodiment, the cavity formed in the proximal surface of the spacer component has a complementary surface and the reconfiguration assembly is operable to transfer torque from the spacer component to the stop component.

In one embodiment, the stop component may include a body defining an axial opening having internal threads complementary to the threading formed on the threaded rod and dimensioned to threadingly engage the threaded rod at a position adjacent the proximal end of the threaded rod. In another embodiment, the stop component may include a body defining an axial opening dimensioned to receive the proximal end of the threaded rod and the body may be welded to the threaded rod at a position adjacent the proximal end of the threaded rod. In yet another embodiment, the stop component may be integrally formed with the threaded rod and include a radial dimension greater than the diameter of the bore formed in the spacer component. In still yet another embodiment, the stop component may include a body defining an axial opening dimensioned to receive the proximal end of the threaded rod, the body including a first radial aperture and the threaded rod including a second radial aperture, and the junction further includes a pin positioned through the first and second apertures to limit relative rotational movement between the threaded rod and the stop component. In another embodiment, the body of the stop component may include an outer dimension, the pin may have a length greater than the outer dimension of the body, and the pin may be positioned such that each of the first and second ends of the pin extend beyond the body of the stop component on respective sides of the body.

In one variation of any of the above-disclosed embodiments, the stop component may further include a proximal flange having a radial dimension greater than the body of the stop component, the cavity formed in the spacer component may be dimensioned to receive the body of the stop component, the spacer component defines a shoulder surface dimensioned to contact the proximal flange and the spacer component defines a radial channel configured to contain the first and second ends of the pin.

In an alternate embodiment, the distal side of the stop component may include a geometric shape defining a plurality of distal surfaces, the cavity formed in the proximal side of the spacer component may include a plurality of contact surfaces dimensioned to complement the plurality of distal surfaces of the stop component such that, when the stop component is received within the cavity, the contact surfaces of the cavity contact the distal surfaces of the stop component and permit torque applied to the spacer to be transferred to the stop component to thereby rotate the threaded rod. In one variation of this embodiment, the distal side of the stop component may include three or more sides.

In another embodiment, the proximal surface of the stop component may be affixed to the driver in a manner whereby the stop component is restricted from separating from the spacer component upon rotation of the driver in a second direction opposite the first direction. In yet another embodiment, the distal surface of the spacer component may be a convex surface and the proximal end of the second member may include a complementary concave surface, wherein the interface is capable of transmitting a compressive force substantially in the direction of a longitudinal axis of the threaded rod from the spacer component to the second member.

As previously mentioned, the reconfigurable bone adjustment device of any of the above embodiments may be an intramedullary limb lengthening nail or an intramedullary bone transport nail. In one embodiment, the first member has a proximal end and a distal end and defines an internal chamber therein, the drive mechanism may be positioned in the internal chamber, the second member has a proximal end and a distal end and at least the proximal end of the second member may be positioned in the internal chamber between the drive mechanism and the distal end of the first member.

In another embodiment, for example, when the reconfigurable bone adjustment device is an intramedullary limb lengthening nail, the proximal end of the first member is configured to be coupled to a first end of a bone and the distal end of the second member is configured to be coupled to a second end of the bone, and rotation of the threaded rod moves the second end of the bone relative to the first end of the bone. The proximal end of the first member may include one or more proximal holes configured to receive one or more screws that pass through the bone and through the one or more proximal holes to attach the first member to the bone and the distal end of the second member may include one or more distal holes configured to receive one or more screws that pass through the bone and through the one or more distal holes to attach the second member to the bone.

In another embodiment, for example, when the reconfigurable bone adjustment device is an intramedullary bone transport nail, the proximal end of the first member is configured to be coupled to a first bone fragment and the distal end of the first member is configured to be coupled to a second bone fragment, the second member is configured to be coupled to a middle bone segment and rotation of the threaded rod moves the middle bone segment relative to the first bone fragment. The proximal end of the first member may include one or more proximal holes configured to receive one or more screws that pass through the first bone fragment and through the one or more proximal holes to attach the proximal end of the first member to the first bone fragment, the distal end of the first member may include one or more distal holes configured to receive one or more screws that pass through the second bone fragment and through the one or more distal holes to attached the distal end of the first member to the distal bone fragment and the second member may include one or more intermediate holes configured to receive one or more screws that pass through the middle bone segment and through the one or more intermediate holes to attach the second member to the middle bone segment.

The present disclosure also contemplates a reconfigurable bone adjustment device in accordance with any of the above embodiments wherein the drive mechanism includes a member selected from the group consisting of an internal rotatable magnet, a motor with induction drive, a battery powered motor and a motor powered through transcutaneous wires. A subset of these embodiments includes embodiments in which the drive mechanism includes an internal magnet configured to be rotated about a longitudinal axis of the threaded rod coupled to the drive mechanism by a magnetic force applied external of the reconfigurable bone adjustment device.

In one embodiment, a system is provided including an embodiment of the reconfigurable bone adjustment device including a drive mechanism having an inner magnet and an external magnetic actuator. The system may also include a transport container for the external magnetic actuator. Kits may also be provided that include any embodiment of the reconfigurable bone adjustment devices or systems disclosed herein and two or more bone screws configured to attach the first and second members to the first and second bone fragments; and kits that include any embodiment of the reconfigurable bone adjustment devices or systems or kits disclosed herein and further comprising one or both of an inserter configured to releasably couple to a proximal end of the reconfigurable bone adjustment device or to a distal end of the reconfigurable bone adjustment device and instrumentation for aligning bone screws, driving bone screws or both.

While the present disclosure has been illustrated and described in detail in the drawings and foregoing description, the same is to be considered as illustrative and not restrictive in character, it being understood that only the certain embodiments have been shown and described and that all changes, alternatives, modifications and equivalents that come within the spirit of the disclosure are desired to be protected.

It should be understood that while the use of words such as preferable, preferably, preferred or more preferred utilized in the description above indicate that the feature so described may be more desirable, it nonetheless may not be necessary and embodiments lacking the same may be contemplated as within the scope of the present disclosure, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

The invention claimed is:

1. A reconfigurable bone adjustment device comprising:
a first member configured for attachment to a first bone fragment;
a second member configured for attachment to a second bone fragment; and
a reconfiguration assembly configured to move the second member relative to the first member, the reconfiguration assembly including:
a drive mechanism including a driver, the drive mechanism operable to controllably rotate the driver; and
a threaded rod having a proximal end operatively coupled to the driver at a junction so that rotation of the drive mechanism rotates the driver, which rotates the threaded rod; and
a collar positioned between the driver and the second member such that rotation of the threaded rod in a first direction exerts a compressive force between a distal surface of the driver and a proximal surface of the collar, and between a distal surface of the collar and a proximal end of the second member, the distal surface of the collar includes a convex surface for contacting a complementary concave surface formed on the proximal end of the second member, the complementary convex and concave surfaces forming an interface for transmitting the compressive force.

2. The reconfigurable bone adjustment device of claim 1, wherein the reconfigurable bone adjustment device is an intramedullary limb lengthening nail.

3. The reconfigurable bone adjustment device of claim 1, wherein the reconfigurable bone adjustment device is an intramedullary bone transport nail.

4. The reconfigurable bone adjustment device of claim 1, wherein the drive mechanism is an internal magnet adapted for rotation via an external magnetic actuator.

5. A reconfigurable bone adjustment device comprising:
a first member configured for attachment to a first bone fragment;
a second member configured for attachment to a second bone fragment; and
a reconfiguration assembly configured to move the second member relative to the first member, the reconfiguration assembly including:
a drive mechanism including a driver, the drive mechanism operable to controllably rotate the driver; and
a threaded rod having a proximal end operatively coupled to the driver at a junction so that rotation of the drive mechanism rotates the driver, which rotates the threaded rod, the threaded rod including a first distal segment having a first diameter and a second proximal segment adjacent the proximal end of the threaded rod, the second proximal segment having a second diameter, the second diameter being greater than the first diameter;
wherein the second proximal segment includes a tapered surface extending from the proximal end of the threaded rod to the first distal segment, rotation of the threaded rod causes the tapered surface of the second proximal segment to contact a proximal end of the second member.

6. The reconfigurable bone adjustment device of claim 5, wherein the reconfigurable bone adjustment device is an intramedullary limb lengthening nail.

7. The reconfigurable bone adjustment device of claim 5, wherein the reconfigurable bone adjustment device is an intramedullary bone transport nail.

8. The reconfigurable bone adjustment device of claim 5, wherein the drive mechanism is an internal magnet adapted for rotation via an external magnetic actuator.

9. A reconfigurable bone adjustment device comprising:
a first member configured for attachment to a first bone fragment;
a second member configured for attachment to a second bone fragment; and
a reconfiguration assembly configured to move the second member relative to the first member, the reconfiguration assembly including:
a drive mechanism including a driver, the drive mechanism operable to controllably rotate the driver; and
a threaded rod having a proximal end operatively coupled to the driver at a junction so that rotation of the drive mechanism rotates the driver, which rotates the threaded rod, the threaded rod including a first distal segment having a first diameter, a second proximal segment adjacent the proximal end of the threaded rod, the second proximal segment having a second diameter, the second diameter being greater than the first diameter, and a third segment having a third diameter, the third diameter being greater than the first diameter and the second diameter; wherein the third segment is located in-between the first and second segments.

10. The reconfigurable bone adjustment device of claim 9, wherein the third segment includes an enlarged spherical segment.

11. The reconfigurable bone adjustment device of claim 10, wherein the enlarged spherical segment includes an articulating surface for contacting a proximal end of the second member.

12. The reconfigurable bone adjustment device of claim 11, wherein the articulating surface of the enlarged spherical segment and the proximal end of the second member include corresponding concave and convex articulating surfaces.

13. The reconfigurable bone adjustment device of claim 11, wherein the articulating surface of the enlarged spherical segment and the proximal end of the second member include corresponding spherical articulating surfaces.

14. The reconfigurable bone adjustment device of claim 9, wherein the reconfigurable bone adjustment device is an intramedullary limb lengthening nail.

15. The reconfigurable bone adjustment device of claim 9, wherein the reconfigurable bone adjustment device is an intramedullary bone transport nail.

16. The reconfigurable bone adjustment device of claim 9, wherein the drive mechanism is an internal magnet adapted for rotation via an external magnetic actuator.

17. A reconfigurable bone adjustment device comprising:
a first member configured for attachment to a first bone fragment;
a second member configured for attachment to a second bone fragment; and
a reconfiguration assembly configured to move the second member relative to the first member, the reconfiguration assembly including:
a drive mechanism including a driver, the drive mechanism operable to controllably rotate the driver; and
a threaded rod having a proximal end operatively coupled to the driver at a junction so that rotation of the drive mechanism rotates the driver, which rotates the threaded rod;
wherein the junction includes a stop component coupled to the threaded rod adjacent to the proximal end of the threaded rod and a spacer component, the spacer component including:
a bore dimensioned to permit passage of the threaded rod therethrough;
a distal surface configured to contact a proximal end of the second member; and
a cavity extending from a proximal side of the spacer component, the cavity dimensioned to receive the stop component therein.

18. The reconfigurable bone adjustment device of claim 17, wherein the cavity formed in the spacer component and the stop component have complementary surfaces so that rotation of the spacer component rotates the stop component.

19. The reconfigurable bone adjustment device of claim 17, wherein the stop component includes a body having an aperture and the threaded rod includes an aperture, the aperture formed in the body and the aperture formed in the threaded rod being aligned with one another for receiving a pin therethrough, the pin includes a first end, a second end, and a length defined by the first and second ends, the length of the pin being greater than an outer dimension of the body so that the first and second ends of the pin extend beyond the body of the stop component, the spacer component including a channel for receiving the first and second ends of the pin when the stop component is received within the cavity of the spacer component, wherein the first and second ends of the pin contact one or more side surfaces of the channel when the driver is rotated so that torque is transferred from the spacer component to the threaded rod.

20. The reconfigurable bone adjustment device of claim 17, wherein the stop component includes a radially extending flange, the cavity formed in the spacer component including a shoulder dimensioned to contact the flange when the stop component is received within the cavity.

21. The reconfigurable bone adjustment device of claim 17, wherein the stop component includes a distal side having a geometric shape defined by a plurality of distal contact surfaces, and the cavity formed in the proximal side of the spacer component includes a plurality of complementary contact surfaces so that, when the stop component is received within the cavity, the contact surfaces of the cavity contact the distal surfaces of the stop component.

22. The reconfigurable bone adjustment device of claim 17, wherein the reconfigurable bone adjustment device is an intramedullary limb lengthening nail.

23. The reconfigurable bone adjustment device of claim 17, wherein the reconfigurable bone adjustment device is an intramedullary bone transport nail.

24. The reconfigurable bone adjustment device of claim 17, wherein the drive mechanism is an internal magnetic adapted for rotation via an external magnetic actuator.

* * * * *